(12) United States Patent
Ciustea et al.

(10) Patent No.: US 9,061,040 B2
(45) Date of Patent: Jun. 23, 2015

(54) COMBINATION THERAPY FOR BREAST CANCER

(71) Applicant: Mihai Ciustea, Westport, CT (US)

(72) Inventors: Mihai Ciustea, Westport, CT (US);
Ghiorghe Ciustea, Bucharest (RO)

( * ) Notice: Subject to any disclaimer, the term of this patent is extended or adjusted under 35 U.S.C. 154(b) by 0 days.

(21) Appl. No.: 14/513,716

(22) Filed: Oct. 14, 2014

(65) Prior Publication Data

US 2015/0094277 A1   Apr. 2, 2015

Related U.S. Application Data

(63) Continuation-in-part of application No. 13/209,653, filed on Aug. 15, 2011, now abandoned.

(51) Int. Cl.

| | |
|---|---|
| *A61K 31/7068* | (2006.01) |
| *A61K 31/661* | (2006.01) |
| *A61K 31/519* | (2006.01) |
| *A61K 31/167* | (2006.01) |
| *A61K 31/593* | (2006.01) |
| *A61K 45/06* | (2006.01) |

(52) U.S. Cl.
CPC ........... *A61K 31/7068* (2013.01); *A61K 31/661* (2013.01); *A61K 31/519* (2013.01); *A61K 31/167* (2013.01); *A61K 31/593* (2013.01); *A61K 45/06* (2013.01)

(58) Field of Classification Search
CPC ............ A61K 31/7068; A61K 31/661; A61K 31/519; A61K 31/167; A61K 2300/00
See application file for complete search history.

(56) References Cited

U.S. PATENT DOCUMENTS

| | | |
|---|---|---|
| 6,559,139 B1 | 5/2003 | Johnson et al. |
| 7,071,158 B2 | 7/2006 | Chinery et al. |

FOREIGN PATENT DOCUMENTS

| | | |
|---|---|---|
| DE | 19721211 A1 | 11/1998 |

OTHER PUBLICATIONS

Bocci, G., K.C. Nicolaou, R.S. Kerbel, Protracted low-dose effects on human endothelial cell proliferation and survival in vitro reveal a selective antiangiogenic window for various chemotherapeutic drugs. Cancer Research, 2002. 62(23): p. 6938-6943.
Browder, T., C.E. Butterfield, B.M. Kraling, B. Shi, B. Marshall, M.S. O'Reilly, and J. Folkman, Antiangiogenic scheduling of chemotherapy improves efficacy against experimental drug-resistant cancer. Cancer Research, 2000. 60(7): p. 1878-1886.
Bertolini, F., S. Paul, P. Mancuso, S. Monestiroli, A. Gobbi, Y. Shaked, and R.S. Kerbel, Maximum tolerable dose and low-dose metronomic chemotherapy have opposite effects on the mobilization and viability of circulating endothelial progenitor cells. Cancer Research, 2003. 63(15): p. 4342-4346.
Colleoni, M., A. Rocca, M.T. Sandri, L. Zorzino, G. Masci, F. Nole, G. Peruzzotti, C. Robertson, L. Orlando, S. Cinieri, F. De Braud, G. Viale, and A. Goldhirsch, Low-dose oral methotrexate and cyclophosphamide in metastatic breast cancer: antitumor activity and correlation with vascular endothelial growth factor levels. Annals of Oncology, 2002. 13(1): p. 73-80.
Klement, G., S. Baruchel, J. Rak, S. Man, K. Clark, D.J. Hicklin, P. Bohlen, and R.S. Kerbel, Continuous low-dose therapy with vinblastine and VEGF receptor-2 antibody induces sustained tumor regression without overt toxicity. Journal of Clinical Investigation, 2000. 105(8): p. R15-R24.
Kakeji, Y. and B.A. Teicher, Preclinical studies of the combination of angiogenic inhibitors with cytotoxic agents. Investigational New Drugs, 1997. 15(1): p. 39-48.
Berd, D., H.C. Maguire, and M.J. Mastrangelo, Potentiation of human cell-mediated and humoral immunity by low-dose cyclophosphamide. Cancer Research, 1984. 44(11): p. 5439-5443.
Munoz, R., S. Man, Y. Shaked, C.R. Lee, J. Wong, G. Francia, and R.S. Kerbel, Highly efficacious nontoxic preclinical treatment for advanced metastatic breast cancer using combination oral UFT-cyclophosphamide metronomic chemotherapy. Cancer Research, 2006. 66(7): p. 3386-3391.
Berd, D. and M.J. Mastrangelo, Effect of low dose cyclophosphamide on the immune system of cancer patients: reduction of T-suppressor function without depletion of the CD8+ subset. Cancer Research, 1987. 47(12): p. 3317-21.
Pili, R., M.P. Kruszewski, B.W. Hager, J. Lantz, and M.A. Carducci, Combination of phenylbutyrate and 13-cis retinoic acid inhibits prostate tumor growth and angiogenesis. Cancer Research, 2001. 61(4): p. 1477-1485.
Carducci, M.A., J. Gilbert, M.K. Bowling, D. Noe, M.A. Eisenberger, V. Sinibaldi, Y. Zabelina, T.L. Chen, L.B. Grochow, and R.C. Donehower, A Phase I clinical and pharmacological evaluation of sodium phenylbutyrate on an 120-h infusion schedule. Clin Cancer Research, 2001. 7(10): p. 3047-55.

(Continued)

*Primary Examiner* — Ruixiang Li

(57) ABSTRACT

The present invention provides therapy and methods for the treatment and prevention of diseases of cell proliferation such as cancer, benign tumors, and viral diseases such as HIV-AIDS, hepatitis B, hepatitis C and cirrhosis. The methods of this invention consist of the administration to a patient of a combination of effective amounts of agents capable of eradicating the neoplastic cells, while sparing the non-neoplastic cells from cytotoxic side-effects. The agents co-administered in therapeutically effective amounts are: chemotherapeutic agents, apoptotic agents, anti-angiogenic agents, cell differentiation agents, immunomodulating agents, antioxidants, vitamins, microelements, enzymes and natural extracts.

14 Claims, No Drawings

(56) References Cited

OTHER PUBLICATIONS

Gilbert, J., S.D. Baker, M.K. Bowling, L. Grochow, W.D. Figg, Y. Zabelina, R.C. Donehower, and M.A. Carducci, A phase I dose escalation and bioavailability study of oral sodium phenylbutyrate in patients with refractory solid tumor malignancies. Clinical Cancer Research, 2001. 7(8): p. 2292-2300.

Gore, S.D., L.J. Weng, W.D. Figg, S.P. Zhai, R.C. Donehower, G. Dover, M.R. Grever, C. Griffin, L.B. Grochow, A. Hawkins, K. Burks, Y. Zabelena, and C.B. Miller, Impact of prolonged infusions of the putative differentiating agent sodium phenylbutyrate on myelodysplastic syndromes and acute myeloid leukemia. Clinical Cancer Research, 2002. 8(4): p. 963-970.

Jones, G., S.A. Strugnell, and H.F. Deluca, Current understanding of the molecular actions of vitamin D. Physiological Reviews, 1998. 78(4): p. 1193-1231.

Majewski, S., A. Szmurlo, M. Marczak, S. Jablonska, and W. Bollag, Inhibition of tumor cell-induced angiogenesis by retinoids, 1,25-dihydroxyvitamin-D3 and their combination. Cancer Letters, 1993. 75(1): p. 35-39.

Yu, W.D., M.C. McElwain, R.A. Modzelewski, D.M. Russell, D.C. Smith, D.L. Trump, and C.S. Johnson, Enhancement of 1,25-dihydroxyvitamin D-3-mediated antitumor activity with dexamethasone. Journal of the National Cancer Institute, 1998. 90(2): p. 134-141.

Grant, W.B. and C.R. Garland, A critical review of studies on vitamin D in relation to colorectal cancer. Nutrition and Cancer—an International Journal, 2004. 48(2): p. 115-123.

Molnar, J., N. Gyemant, I. Mucsi, A. Molnar, M. Szabo, T. Kortvelyesi, A. Varga, P. Molnar, and G. Toth, Modulation of multidrug resistance and apoptosis of cancer cells by selected carotenoids. In Vivo, 2004. 18(2): p. 237-244.

Weber, T., M. Lu, L. Andera, H. Lahm, N. Gellert, M.W. Fariss, V. Korinek, Vitamin E succinate is a potent novel antineoplastic agent with high selectivity and cooperativity with tumor necrosis factor-related apoptosis-inducing ligand (Apo2 ligand) in vivo. Clinical Cancer Research, 2002. 8(3): p. 863-869.

The effect of vitamin E and beta carotene on the incidence of lung cancer and other cancers in male smokers. The Alpha-Tocopherol, Beta Carotene Cancer Prevention Study Group. New England Journal of Medicine, 1994. 330(15): p. 1029-35.

Jacobs, E.J., A.K. Henion, P.J. Briggs, C.J. Connell, M.L. McCullough, C.R. Jonas, C. Rodriguez, E.E. Calle, and M.J. Thun, Vitamin C and vitamin E supplement use and bladder cancer mortality in a large cohort of US men and women. American Journal of Epidemiology, 2002. 156(11): p. 1002-1010.

Wilt, T.J., A. Ishani, G. Stark, R. Macdonald, J. Lau, and C. Mulrow, Saw palmetto extracts for treatment of benign prostatic hyperplasia—A systematic review. Jama-Journal of the American Medical Association, 1998. 280(18): p. 1604-1609.

COMBINATION THERAPY FOR BREAST CANCER

CROSS-REFERENCE TO RELATED APPLICATIONS

This application is a continuation-in-part of U.S. application Ser. No. 13/209,653 filed on Aug. 15, 2011.

STATEMENT REGARDING FEDERALLY SPONSORED RESEARCH OD DEVELOPMENT

Not Applicable

REFERENCE TO SEQUENCE LISTING, A TABLE, OR A COMPUTER PROGRAM LISTING COMPACT DISC APPENDIX

Not Applicable

FIELD OF THE INVENTION

The present invention generally relates to a method for treating hyperproliferative diseases, particularly cancer. Specifically, the method of the invention involves the co-administration to a patient, such as a warm-blooded animal, including human, of an effective combination of agents with multiple effects on the cancer and its host.

BACKGROUND OF THE INVENTION

To date, cancer treatment has been unsatisfactory. Despite the large number of anticancer therapies that have been investigated in clinical trials and the advances made in chemotherapeutic regimens, cancer treatment today is inadequate: it is not very effective and has major side effects. There is a significant unmet medical need for clinically effective, nontoxic treatments of cancer that overcome the drawbacks of conventional therapies. We need therapies with increased efficacy and reduced toxicity that can completely eliminate malignancies, ensure survival and provide patients with a better quality of life during and after treatment.

The abnormal vasculature of tumors and the resulting abnormal microenvironment are a barrier to the delivery and efficacy of antineoplatic agents. Tumor vessels have large holes in their walls, and their leakiness leads to increased interstitial pressure as well as nonuniform blood flow. Impaired blood supply and high interstitial fluid pressure interfere with the delivery of therapeutics to tumors. Hypoxia (low oxygen concentration) makes tumor cells more resistant to radiation and several cytotoxic drugs. Hypoxia also induces genetic instability and selects for cells with increased malignancy. In addition, hypoxia and low pH compromise the functions of cytotoxic immune cells.

Antiangiogenic therapies can prevent the formation of new blood vessels in and around tumors. They normalize the tumor vasculature and increase its efficiency, thus increasing the tumor uptake of drugs and oxygen, and distributing them to a larger fraction of the tumor cells. Increased penetration of drugs throughout the tumor enhances the outcome of therapy, and increased levels of oxygen enhance the efficacy of radiation and chemotherapeutic agents.

The endothelial cells that make up the tumor's blood supply are highly proliferative and are very sensitive to low doses of cytotoxic agents. Many traditional chemotherapeutics act as antiangiogenic drugs, as they affect these rapidly proliferating endothelial cells from tumor vessels. For example, cyclophosphamide, methotrexate, vinblastine, and paclitaxel have antiproliferative effects on endothelial cells at concentrations 10- to 100,000-fold lower than those required for inhibition of proliferation of tumor cells, epithelial cells, lymphocytes and fibroblasts [1]. The activated endothelial cells are genetically stable and might not develop drug resistance. Also, most normal vasculature in adults is relatively quiescent and not affected by antiangiogenic therapies.

Metronomic chemotherapy refers to the close, regular administration of relatively low doses of cytotoxic drugs, with minimal or no drug-free breaks, over prolonged periods. Low doses of chemotherapeutic drugs (metronomic dosing) affect tumor endothelium and inhibit tumor angiogenesis. Activated endothelial cells are more sensitive to protracted, low-dose chemotherapy compared to tumor and normal cells [1]. Metronomic dosing of cyclophosphamide, 5-fluorouracil and other cytotoxic drugs was shown to be antiangiogenic [2].

The antiangiogenic effect of chemotherapy and radiation might also be mediated by impairing the mobilization, function or viability of circulating endothelial cells and endothelial progenitor cells released from the bone marrow. Circulating endothelial progenitor (CEP) cells can be mobilized from the bone marrow, enter the peripheral circulation, home in on sites of ongoing angiogenesis, incorporate into the lumen of growing sprouts, and differentiate into endothelial cells. These cells seem to be direct targets of chemotherapy, independent of whether the drugs are used in a maximum tolerated dose (MTD) or metronomic fashion [3]. CEP cell levels decrease markedly and abruptly when MTD chemotherapy is administered, but rebound rapidly during the break period between doses. This is similar to the hematopoietic rebound of other bone marrow precursor cells that are similarly affected, such as those in the granulocytic and thrombocytic lineages. Although the contribution level of marrow-derived CEPs to angiogenesis is not known, the continuous suppression of these cells could represent a major component of the antiangiogenic mechanisms of metronomic chemotherapy.

The radiation oncology community has long understood that frequent low doses offer a better therapeutic outcome than do less frequent higher doses. Whereas surprisingly durable and potent tumor responses have been observed in a number of preclinical tumor models, relapses usually occur with metronomic administration of chemotherapy. In general, chronic low-dose chemotherapy alone has not led to long-term cure of drug-resistant tumors, and metronomic regimens did not significantly improve overall survival in heavily pre-treated patients. Clinical studies in patients with metastatic colon cancer showed a higher response rate with continuous-infusion therapy (22% vs. 14%), but the impact on survival was minimal. Other clinical trials with low-dose or continuous-infusion chemotherapy have had limited success. There are, however, encouraging anecdotal results: for example, in a study in which drug-resistant patients with breast cancer were placed on a low-dose metronomic schedule of the same cytotoxic drug [4]. Metronomic treatments also have other advantages, such as marked cost savings and improved cost-effectiveness.

BRIEF SUMMARY OF THE INVENTION

The present invention provides methods for the prevention and treatment of cancer and other neoplastic disorders. In one aspect, the invention provides therapies useful for the treatment of cancer in mammals and more specifically in humans. The method of this invention involves co-administration to the mammal of a combination of agents in therapeutically effective amounts: anti-neoplastic agents, chemotherapeutic agents, apoptotic agents, anti-angiogenic agents, cell differentiation agents, immunomodulating agents, antioxidants, enzymes, vitamins, microelements and natural extracts. An advantage of the invention is that many of the drugs and agents of the therapy have already been shown to be safe and well-tolerated during chronic administration in humans. A further advantage of the invention is that one or more drugs previously tested in clinical trials and found to be safe, but by themselves not efficacious enough to be approved for cancer therapy, prove to be effective when used in the context of the combination therapy. The invention's differentiation from other treatments, in part, may be considered a result of the use of ingredients that, when combined, provide effects against cancer cells that may fall outside of, or in addition to, the logical expectation of any single ingredient.

DETAILED DESCRIPTION OF THE INVENTION

The present invention provides methods for the treatment and prevention of hyperproliferative (e.g. cancers, including solid tumors and leukemias, psoriasis, etc) and viral disorders (e.g., hepatitis B, hepatitis C, HIV-AIDS). The disorders caused by cell hyperproliferation are diverse and have various pathologies. They can be of oncological nature, such as malignant neoplasias, or non-oncological nature, such as benign tumors, psoriasis, etc. The methods of this invention can be used for the treatment and prevention of any disorder of cell proliferation or cell differentiation (malignant or non-malignant). The methods of this invention can be used for the treatment of cancer, drug-resistant cancer or radiation-resistant cancer. The methods of this invention can also be used to sensitize a subject to other therapies, such as radiation therapy, or can be used as maintenance therapy of cancer patients. The methods of this invention can be used for the treatment and prevention of viral infections (where the virus may be a retrovirus, such as the human immunodeficiency virus), for the treatment and prevention of AIDS and AIDS-associated dysfunctions (such as central nervous system dysfunctions), to enhance immunosurveillance, etc. The methods of this invention can be used to treat animal subjects, including warm-blooded animals, particularly humans.

It is an object of this application to provide anticancer therapies that have the potency to eradicate neoplastic cells at multiple sites in the body and spare non-neoplastic cells from cytotoxic side effects. The methods of this invention are effective for the treatment of mammals with both primary and disseminated cancers. By devitalizing the cancer cells, the therapy reduces their ability to metastasize and disseminate. In addition to reducing the sizes of the tumors already present, the treatment eliminates the potential for further spread of neoplastic cells and formation of new metastases.

The methods of this invention comprise the administration of combinations of agents that together are highly effective for the therapy of cell-proliferating and viral diseases. The present invention is based on the surprising discovery that appropriate dosages of combinations of several agents and compounds, some of them well-known for the treatment of cancer and other diseases, result in a very effective therapy that has no significant side effects. Administration of the combination described herein results in a spectacular reduction of tumor size or neoplastic cell numbers in the patient.

The biological functions of the agents used in the combinations described herein are complimentary and overlapping. By having overlapping activities, agents can replace and potentiate each other to achieve the desired functions. The use of multiple agents with overlapping activities results in synergistic effects toward fulfilling the intended biological functions. Combinations of compounds with similar structures and activities are often more effective than any individual component of the combination by itself, even when the single component is administered in larger doses. This general principle applies very well to cancer therapy. Combinations of agents that work synergistically are more effective against cancer cells than any one agent by itself. We have found that the combinations of agents described herein have a strong and synergistic anti-neoplastic effect. The synergy of the combination generates an anti-cancer effect that greatly exceeds the sum of the effects of each component administered individually at optimal or maximum tolerated doses. The cytotoxic effect on cancerous cells is significantly enhanced and the normal healthy cells do not suffer major unwanted side effects. This results in better long-term success rates for cancer patients than any single-agent therapy can provide.

When administered to a patient, the combination therapy of this invention has a complex effect on neoplastic cells inhibition of proliferation, inhibition of angiogenesis, growth arrest, promotion of differentiation, induction of apoptosis, etc. At the same time, the therapy of this invention includes agents that affect the normal non-neoplastic cells of the patient, agents that stimulate, fortify and modulate the immune system and the organism's own defense, and agents that protect healthy cells from the harmful effects induced by the anti-neoplastic drugs.

Through its complex effect on individual neoplastic cells and the whole organism, the combination therapy of this invention substantially reduces or completely eliminates the number of malignant cells in the affected patient. Reduction of the number of viable cells within tumors leads to partial or complete destruction of these tumors. The effects of the treatment can vary from attenuation of cancer progression, delay or slowing of disease progression, palliation or stabilization of the disease state, alleviation or amelioration of one or more symptoms of the disease, shrinkage of tumors, decline in the extent of disease, and prolonged survival, to partial or complete remission of the disease and all of its symptoms. In most cases, the combination therapy results in tumor regression and complete disease remission. Reduction in the patient's tumor burden results in attenuation of cancer's pathogenic effects, alleviation of general malaise and improvement of the patient's general state. The potent anti-neoplastic effect and lack of harmful side effects result in an improved quality of life for the patient during and after therapy.

The methods of this invention have unexpected advantages and are highly successful in the treatment of diseases that involve cell proliferation. The anticancer therapy of this invention is successful because it has a multitude of effects on cancer cells and host. It devitalizes the neoplastic cells, inhibits their proliferation, inhibits their invasion and metastatic dissemination to other parts of the body, strengthens the host and enhances its immune response, protects healthy cells and tissue from the deleterious effects of cancer.

It is generally accepted that cancer cells are more sensitive to combinations of anticancer agents than to single agents. Co-administration of multiple agents provides a better therapeutic result for both drug-resistant and drug-sensitive cancers. The combination therapy of this invention is effective against cancers that are otherwise resistant to current standard therapies. The combination therapy is working not only for previously untreated patients, but also for patients that had undergone anti-cancer treatments and present with cancers that are refractory to other therapies, such as chemotherapy or radiotherapy. Furthermore, the method of the invention prevents cancers from acquiring resistance to the ongoing therapy. In contrast, conventional therapies use single agents or combinations of few agents and induce development of resistance.

The therapeutic methods of this invention avoid the heavy use of any agent, while providing excellent therapeutic benefits. The combinations of agents of this invention are highly effective in the therapy of cancer probably because of the cumulative and synergistic effects of agents on cancer cells. The high efficacy of the combination results in an increased anticancer activity and allows for the administration of low doses of each agent. As each cytotoxic component of the combination is administered in amounts well below those used in conventional therapy, the harmful side effects are minimal. The toxic side effects of the agents of this combination are not overlapping and the unwanted damage to any single organ is minimal. Healthy tissue can easily repair small injuries, while cancer cells do not have the capacity to recover from the cumulative effect of multiple agents. In addition to using doses of agents that are non-toxic, the combination contains components that potentiate the efficacy of anticancer agents, reduce their toxicities and protect normal cells and tissue from harmful side effects. The lack of adverse side effects and reduction of tumor burden leads to improvement in the quality of life of patients, encourages the patients' compliance with the therapy and avoids hospitalizations and adjuvant treatments commonly needed during cytotoxic therapies.

This therapy can also be used for cancer prevention, especially in people who might have a high risk or predisposition to cancer, or for maintenance and prevention of recurrence in patients who are considered in remission and might have residual disease. The therapy has beneficial characteristics that make it suitable for cancer prevention and remission maintenance: it has anticancer effects, it is not toxic, it is well tolerated and easy to administer over long time periods, it is inexpensive.

The therapeutic methods of this invention have beneficial effects also when administered together with other anti-cancer therapies. These additional therapies may be administered to the patient before, after or simultaneously with the therapy of this invention. The other anticancer therapy should have some utility to the patient, as determined by a person of ordinary skill in the art. For example, the combination therapy of the present invention can be accompanied by the administration of other chemotherapeutic or anti-cancer agents, radiation therapy, immunotherapy, hormonal therapy, gene therapy, surgery, antiangiogenic therapy or alternative therapies. The association of the therapy of this invention to conventional anticancer therapies strengthens the efficacy of these therapies and has beneficial effects: it limits the occurrence of resistance, limits the metastasizing effect of surgical or irradiation stress, etc.

Also included within the scope of the present invention is the co-administration of the therapy of this invention, or of components of the therapy, in conjunction with other agents, such as hormones, antiangiogenic agents, antimetabolites, alkylating agent, platinum agents, antibiotics, antimicrotubule agents, topoisomerase inhibitors or any other anticancer agent. It is, of course, contemplated that the combination therapy of this invention may be used with other therapies not yet in practice.

The combination of agents of the therapy of this invention can be administered together with other agents that treat or prevent other diseases or symptoms in the patient. These agents include, but are not limited to, antiviral agents, antibiotics, antifungal agents, anti-inflammatory agents, antithrombotic agents, cardiovascular agents, hypertension drugs, cholesterol-lowering agents, and others. It is to be understood that such other agents should not interfere with, nor adversely affect the combination therapy of this invention.

The combination therapy of this invention can be supplemented with radiation therapy, as administration of the therapy improves the therapeutic outcome of ionizing radiation. Some components of the combination therapy of this invention have radio-sensitizing effects on cancer cells and make the tumors more susceptible to radiation. Some other components of our therapy protect normal tissue from the harmful effects of radiation and increase the ability of normal tissue to withstand the effects of radiation. Increase or restoration of the sensitivity of cancer cells to radiation and protection of normal cells are highly advantageous effects. The anticancer effects of our therapy and radiotherapy are synergistic (the therapeutic efficacy is greater than additive). When combined with the therapy, radiation should be administered at lower doses and less frequently than in the common radiotherapy regimens. The combined administration of these therapies is highly effective against cancer, even at low doses of radiation, and the adverse side effects characteristic of radiotherapy are avoided.

Hormonal therapy may also be used in conjunction with the therapy of the present invention. Certain cancers, such as breast, prostate, or ovarian cancers, are partially responsive to hormonal therapy.

The therapy of this invention may be co-administered with and improved by antiangiogenic drugs. Antiangiogenic drugs augment the antivascular effects of the therapy. Therapy with antiangiogenics may sensitize the endothelial cells to cytotoxic agents and potentiate the effects of the therapy. For example, drugs that target the vascular endothelial growth factor (VEGF) survival pathway of endothelial cells (e.g., bevacizumab) are synergistic with chemotherapies that target the endothelium [5]. The antiangiogenic agents are more effective adjuvants to cytotoxic therapies when used as two-agent combinations, rather than as single agents [6]. By themselves, current antiangiogenics are unable to maintain vascular regression durably, as evidenced by clinical observations of tumor relapse and return to abnormal new vessel formation in tumors.

The preferred mode for the administration of the agents for systemic delivery is oral. Preferably, the combination is administered orally at doses recommended in this application, but the agents can also be formulated for other administration routes, such as parenteral administration (intravenous, intramuscular, subcutaneous, intrauterine), submucosal administration, infusions and others. The term "co-administration" refers to any administration route in which two or more agents are administered to a patient or subject. The agents may be administered simultaneously or sequentially. They may be administered together, before or after each other. The agents may be administered individually or as mixtures (two or more agents combined in the same capsule). The active ingredients may be administered at once or may be divided into a number of smaller doses to be administered at varying intervals of time. The daily dose of each agent may be administered once a day in a single dosage or may be divided in subdoses and administered multiple times during the day (two, three, four or five times per day). Also, a modified-release form of the compounds may be used. Generally, the compounds of this invention are dispensed by unit dosage formulated in a pharmaceutically acceptable carrier.

The majority of compounds of the combination therapy have been extensively used in humans. The dosage, schedule and duration of administration of compounds and agents of the claimed combination therapy depend on many factors, including: the agent, its formulation, the timing and mode of administration, the patient's age, body weight, health, clinical condition and medical history, the patient's response to therapy, the patient's pharmacogenomic profile (effect of genotype on the pharmacokinetic, pharmacodynamic or efficacy of a therapeutic), the condition or the type of cancer being treated, the severity of the condition to be alleviated, the therapeutic goal (e.g., therapy, prophylaxis), administration of co-treatments, the experience and judgment of the clinician or practitioner administering the therapy, and other factors. It is to be understood that for any particular subject, specific dosage regimens should be adjusted according to the individual need and the professional judgment of the person administering or supervising the administration of the treatment, and that the dosage ranges set forth herein are for illustration only and are not intended to limit the scope or practice of the claimed therapy. Also, doses should be adjusted if substitute compounds are used. It will be appreciated that the administration and dosing schedule may be adjusted during the course of the therapy according to the individual patient's need, the response to the therapy, drug tolerance in the event of toxicity and side effects, and the professional judgment of the person administering or supervising the administration. Although this combination therapy is minimally toxic, dosages can be reduced if severe side effects occur. Dosage amounts and intervals can be adjusted individually to provide plasma levels of the active agents that are optimal for obtaining the desired effects.

The dosages described in this patent application were found to be effective for cancer therapy in human adult patients, but these dosages can vary within some limits and can be adjusted for the individual requirements of each particular case. Those of ordinary skill in the art will readily optimize effective doses, formulations, and co-administration regimens in view of an individual patient's conditions. Using doses outside the specified ranges is also within the scope of the broader aspects of this invention.

When administered in the combination therapy of this invention, the therapeutically effective amount for each compound is generally lower than the amount that would be therapeutically effective if the compound were administered alone. As a result, the agents and compounds of the therapy are administered at lower doses than the conventional doses administered in current therapeutic protocols.

For therapeutic and prophylactic applications, the therapy can be administered a single time or many times over periods as long as a month to several months or several years. Long-term administration that may even last for the life of the patient may be indicated in some cases.

A therapeutically effective amount is an amount of the administered agent that results in an objectively identifiable improvement of the subject's condition, as judged by a qualified observer. Improvement of a patient's condition can be anything from: attenuation of symptoms, slowing, reduction or regression of tumor growth and metastasis, improvement of the test or analysis results that indicate the disease evolution (such as tumor-specific markers), increase of the duration of survival of a patient following detection of cancer; complete regression of the cancer, etc. While undergoing the therapy, patients should be monitored in a manner deemed appropriate by the treating physician. A very reliable and fast indicator of the response to therapy is a change in the levels of tumor-specific markers in the patient's blood. Another indication that the therapy is effective is the softening of tumor(s) and a decrease in the diameter of tumor(s), but this is generally noticed after a few weeks to months of therapy.

The multi-component therapy of this invention consists of agents that function through a multitude of mechanisms to: inhibit the growth and proliferation of cancer cells, stimulate and modulate the immune system to eliminate transformed cells and viruses, preserve and promote the functions of normal cells, restore and repair damaged tissue. The therapy combines multiple agents that together achieve a high anti-neoplastic activity and effectively induce remission of the disease.

The majority of agents used in the method of this invention have been researched extensively in pre-clinical and clinical studies. Their pharmacology and toxicology profiles are well established. Many mechanisms of action at molecular and cellular levels have been identified and biological functions have been revealed. For most agents, more than one biological function is known. Every agent of the combination can exert its anti-cancer activity through multiple mechanisms of action. In many cases it is hard to identify exactly what mechanism is responsible for the anti-neoplastic activity, but that seems to depend very much on the specifics of the study: in vivo or in vitro, type of cancer or cells tested, agent concentration, timing and duration of the treatment, and many other parameters. For example, most cytotoxic agents at low concentrations induce cell death by apoptosis, while at higher concentrations they cause cell death through necrosis or some other, yet unknown, mechanism. Moving beyond laboratory experiments, it is even harder to identify exactly the mechanisms that are important for an agent's anti-cancer activity in the actual patient. One example of an agent for which multiple mechanisms have been identified is cyclophosphamide. Initially selected for its cytotoxic properties, cyclophosphamide alkylates and modifies DNA, which most often leads to cell death by apoptosis or necrosis. At the same time, cyclophosphamide has immune-stimulating activity when administered in small doses [7].

Based on their cellular and systemic effects, the agents of the present invention can be classified as antiangiogenic, inductors of apoptosis, inductors of differentiation, modulators and activators of immune response, enhancers of the anti-neoplastic activity of other agents, protectors of healthy cells and tissue, promoters of repair and recovery of normal cells and organs. Some components of the therapy, such as the natural products, contain multiple active ingredients, with many of the ingredients having more than one biological function.

The metronomic administration of the agents of this combination therapy has an inhibitory effect on the endothelial cells recruited at tumor sites and activated to grow the tumor vasculature. These unmutated cells are very sensitive to protracted exposure to low concentrations of some of the agents of the combination therapy. An antiangiogenic mechanism that affects these non-cancerous, stable cells could explain why the combination therapy is active against most cancer forms and does not lead to development of resistance.

There are hundreds of different types of cells in the human body, and they all originate from a single cell. The process by which every cell becomes a specific type is called differentiation. Cell differentiation is highly regulated and ends with the formation of terminally differentiated cells that are specialized in performing specific biological functions. These terminally differentiated cells have lost most of the capacity to proliferate.

Neoplastic cells do not respond to regulators of proliferation and escape the normal control mechanisms associated with growth and differentiation. Some types of cancer cells show many similarities with normal, undifferentiated cells. These cancer cells appear to be blocked in an undifferentiated state, unable to enter a differentiation program. Neoplastic immature cells retain the potential to differentiate and, occasionally, some cancer cells undergo spontaneous differentiation and lose the capacity to proliferate. The differentiation process can be exploited in cancer therapy by taking advantage of the normal mechanisms responsible for cell regulation and differentiation. Cancer cells can be induced to approach or revert to normal cells, which stops their proliferation and brings about decarcinogenesis or reversal of malignancy.

Differentiation therapy is based on the induction of terminal differentiation of neoplastic cells with factors that cause the cancer cells to mature and lose their neoplastic nature. Differentiation therapy is a more desirable approach to treating cancer than killing the cells with cytotoxic agents.

Although many compounds are able to induce differentiation and alter the phenotype of cancer cells in vitro (cyclic AMP, retinoids, aclarubicin and other anthracyclines), their clinical applications are limited by unacceptable toxicities, potential for carcinogenesis, or inability to maintain an effective plasma concentration. Examples of agents that can induce differentiation of cancer cells include: (a) retinoic acid, retinoids and their derivatives (shown to induce the differentiation of immature promyelocytic cells and used in the treatment of acute promyelocytic leukemia), (b) vitamin D analogs, (c) hormones, such as glucocorticoids, (d) proteases, (e) ligands of the peroxisome proliferator-activated receptors and peroxisome proliferators, such as phenylacetate (PA), phenylbutyrate (PB), clofibrate, (f) histone hyperacetylators, such as butyrate or propionate. Other differentiation inducers that are capable of altering the phenotype of cancer cells in vitro include: dibutyryl cyclic adenosine 3',5'-monophosphate, 5-azacytidine, interferons, hexamethylene bisacetamide (HMBA), dimethyl formamide (DMF), dimethyl sulfoxide (DMSO), 12-tetradecanoylphorbol-13 acetate (TPA), etc.

The forms of cancer that most easily respond to differentiation therapy include neuroblastoma and malignant melanoma. Neuroblastoma is a malignant tumor of the childhood that has a very high rate of spontaneous differentiation. Several agents, such as phenylacetic acid (PAA) and retinoic acid (RA), can promote differentiation of neuroblastoma cells into a variety of cells with neural-crest lineage, but these agents have only limited efficacy in the clinical treatment of the disease. Malignant melanoma, which is generally resistant to conventional therapies, can respond to differentiation therapy.

A number of agents have been used to induce differentiation and maturation of cancer cells. Many of these agents are agonist ligands of nuclear receptors that bind and activate transcription factors, leading to regulation of extensive sets of genes. The nuclear receptors regulate many aspects of cell proliferation and differentiation, and play major roles in embryonic development and organism homeostasis. Nuclear receptors control the expression of many genes and their disruption is involved in a broad range of diseases. The mechanisms by which nuclear receptors control gene expression very often involve the formation of receptor homo- or heterodimers. Many examples are known in which nuclear receptors that have different ligands and belong to different subfamilies function together in the same signaling cascade or are present in the same transcription complex. Generally, the control and expression of genes require the activation of more than one type of nuclear receptors in a cooperative mechanism. In view of these mechanistic models, it is not surprising that many synergies between nuclear receptor ligands have been observed.

The combination therapy of the present invention includes agents whose function is to potentiate the antitumor activity of cytotoxic agents. They enhance tumors' and cancer cells' sensitivity to cytotoxic drugs and radiation. The combination therapy of the present invention also includes agents that are able to protect the non-neoplastic cells and tissue from the damage caused by cytotoxic agents and radiation. They prevent the harmful side-effects induced by toxic agents on normal cells, stimulate the restoration of cellular functions, and increase the general detoxification capacity of the organism and the non-specific resistance to toxic agents. The protective and regenerative components of the combination of the present invention increase the general body resistance to harmful agents, such as radiation, toxic substances or infectious agents (bacteria, viruses, fungi). As a result, debilitating side effects and secondary therapy-induced disease commonly associated with cancer therapy are prevented, and the patient's quality of life and recovery are much improved.

Some agents of the therapy of the present invention are known biological response modifiers (immune response modulators and potentiators). Biological response modifiers are immuno-modulating agents that modify the relationship between the tumor and host by strengthening the host's biological response to tumor cells. They potentiate the immune response to the neoplasm and enhance the immunological competence of the patient to indirectly inhibit the growth of cancer cells. They also increase the non-specific body resistance to a variety of agents, such as infections and toxic substances.

Each of these agents of this therapy is discussed separately. A preferred combination of these agents is mentioned. However, all the various permutations and combinations of the individual agents should be understood as encompassed by this disclosure.

Antimetabolites are agents toxic to proliferating cells that are actively going through replication cycles. Actively proliferating cells need a continuous supply of nucleic acids, amino acids, and other cellular constituents. Antimetabolites interfere with the normal biosynthesis or use of these vital cellular constituents and induce cell growth arrest.

Antimetabolites belong to many chemical families. The antimetabolites used in the therapy of this invention are pyrimidine derivatives and antifolates. One antimetabolite can be a fluoropyrimidine, such as 5-fluorouracil (5-FU) or its prodrugs or derivatives. 5-FU and the other fluoropyrimidines exert their cytotoxic effects through multiple mechanisms inhibition of thymidylate synthase (TS), inhibition of DNA synthesis, incorporation into RNA and DNA, etc. 5-FU-based drugs also inhibit tumor progression through inhibition of angiogenesis, mostly by affecting the peritumoral endothelial cells.

The therapy preferably uses 5-FU and its prodrugs or fluoropyrimidines that are suitable for oral delivery, such as capecitabine (N4-pentyloxycarbonyl-5'-deoxy-5-fluorocytidine), 5-fluoro-2'-deoxyuridine (5-FdUrd), ftorafur ([R,S-1-1(tetrahydrofuran-2-yl)-5-FU], FTO, tegafur or futraful), ftorafur's combinations with other drugs. Ftorafur is commonly combined with dihydropyrimidine dehydrogenase (DPD) inhibitors, such as uracil (to make UFT), 5-chloro-2, 4-dihydroxypyridine (gimeracil, gimestat) and a pyrimidine phosphoribosyltransferase inhibitor such as oxonic acid (OXO; otastat) (to make the drug called S-1).

When used in combination therapies, 5-FU has a more favorable effect than when used alone. 5-FU enhances the anticancer activity of other agents, such as cyclophosphamide (CP). Combining 5-FU with agents that induce apoptosis through other mechanisms, such as α-tocopheryl succinate, results in more effective induction of apoptosis of cancer cells. A low-dose metronomic chemotherapy combination of UFT and CP is more effective than the respective monotherapies. This metronomic therapy has a preferential antimetastatic effect, being more inhibitory on the growth of micrometastases than on established primary tumors [8].

The administration schedule of fluoropyrimidines affects cell sensitivity and development of resistance. Cancer cells resistant to intermittent short exposure to 5-FU were shown to be sensitive to continuous exposure, but cells resistant to continuous exposure were also resistant to short-term exposure.

Methotrexate (amethopterin) is an antimetabolite analog of folic acid. Methotrexate can be substituted in the therapy with any antimetabolite analog of folic acid: aminopterin, trimethoprim, pyrimethamine, pemetrexed, raltitrexed.

Alkylating agents achieve their anti-neoplastic activity via multiple mechanisms. Cyclophosphamide (CP) is an oxazaphosphorine prodrug that is converted into products that covalently bind to nucleic acids and proteins. This leads to inhibition of DNA synthesis, cell growth arrest, apoptosis and/or necrosis. Low concentrations of alkylating agents that cannot inhibit DNA synthesis are still able to stop cell growth, and the arrested cells eventually undergo apoptosis.

At low doses, CP has a tumor antiangiogenic effect. Depending on the administration schedule (maximum tolerated dose or metronomic low-dose), CP has opposite effects on the mobilization and viability of circulating endothelial progenitor (CEP) cells. Metronomic administration is associated with decreased CEP numbers and viability [3]. Low-dose CP induces selective apoptosis of endothelial cells within the vascular bed of tumors. CP has been administered in low-dose, metronomic regimens to many cancer patients, by itself or in combination with other antineoplastic agents. The results are promising, but not outstanding.

CP has immuno-modulating activities. At low dose, CP is an immune enhancer and sensitizes established tumors to immunotherapy. CP induces a transitory immunostimulatory effect and reduces the suppression of the immune system by tumors. At low concentration, CP is toxic to suppressor T-cells (it decreases both the number and function of suppressor T-cells), but not to helper T-cells. Low-dose metronomic CP in cancer patients strongly curtails the immunosuppressive regulatory T-cells, whose function is to inhibit the effector T-cells and natural killer (NK) cells [9]. Impairment of suppressor T-cells leads to stimulation of NK cells and restoration of the proliferation and innate killing activities of peripheral T-cells, resulting in a better control of tumor progression.

CP can be substituted in the therapy with other alkylating agents, such as ifosfamide, trofosfamide, glufosfamide.

Retinoids and rexinoids are small molecules with pleiotropic effects. They are a large family of molecules encompassing over three thousand members. Retinoids have a great influence on cell survival, proliferation, differentiation and apoptosis. They can induce cell differentiation and contribute to defining the fates of certain cells during development.

In vitro, retinoids inhibit the proliferation of many cancer cell lines. Retinoic acid is a potent promoter of differentiation in a variety of human neuroblastoma cell lines. Retinoids induce the maturation of acute promyelocytic leukemia (APL) cells and induce tumor regression in some animal models. Leukemic cells in the early stages of differentiation are resistant to apoptosis, but after exposure to differentiation inducers, such as all-trans retinoic acid (ATRA), they stop growing and eventually die by apoptosis.

Retinoids have been used clinically in the treatment of hyperproliferation disorders, such as acute myeloid leukemia and cutaneous T-cell lymphoma. Retinoids have also been used for the treatment of a variety of skin conditions, such as acne, wrinkles, psoriasis, age spots and discoloration. Most notably, retinoids are used in the treatment of APL, a subtype of acute myeloid leukemia. Despite a complete remission rate of about 90%, most patients with APL relapse and are resistant to further treatment with RA. This resistance is partially due to an increased systemic catabolism of RA. Co-administration of the retinoid 4-hydroxyphenylretinamide (4-HPR, Fenretinide) results in inhibition of RA catabolism. 4-HPR increases the biological half-life of RA, markedly enhances RA-induced differentiation, and increases the level of retinoylation, the covalent binding of RA to proteins.

The use of retinoids for cancer prevention is impeded by their toxicity over long-term administration. Administration of high doses of retinoic acid over long periods results in accumulation of retinyl esters in the liver and is associated with hepatic toxicity. 4-HPR seems to be one of the most active and least toxic retinoids. Patients tolerate 4-HPR extremely well with minimal side effects. This is in contrast to the cis-RA-treated patients, who experience a multitude of toxicities.

The biological activities of retinoids and their metabolites are both dependent on and independent of retinoid receptors present inside the cells. Binding of ligands such as RA to these receptors induces activation of specific genes and results in terminal differentiation and growth arrest of cells. Retinoids can also induce rapid cell death, through mechanisms that are receptor-independent. Retinoids modulate the methylation of DNA and have direct effects on cell's secondary messengers. The activity of retinoids might be mediated through an immune response. For example, 4-HPR treatment can reduce the levels of insulin-like growth factor I (IGF-I), an important factor in the pathogenesis of different solid tumors. ATRA can suppress the activity of tumor necrosis factor $\alpha$ (TNF$\alpha$) on white blood cells. TNF$\alpha$ is a mediator of inflammation and its inhibition is effective for the treatment of immuno-inflammatory or proliferative skin diseases. Another possible mechanism for the antiproliferative effects of retinoids is the generation of ceramide, an intracellular lipid that mediates cell death through apoptosis and necrosis.

Retinoids can modulate the effect of antineoplastic drugs and enhance the effect of chemotherapy. Multiple in vitro studies on leukemic cell lines have shown that sequential exposure to a DNA-damaging agent, followed by a differentiation inducer, leads to enhanced cell apoptosis.

Retinoids are more effective when used in combination with other differentiation inducers, and the effects of such combinations are either additive or synergistic. In tumor xenografts of prostate cancer, the combination of phenylbutyrate (PB) and 13-cis retinoic acid (CRA) decreased in vivo tumor cell proliferation, increased apoptosis rate and reduced microvessel density, having a direct effect on both tumor and epithelial cells [10]. The combination of 12-O-tetradecanoylphorbol-13-acetate (TPA), ATRA, 1$\alpha$,25-dihydroxyvitamin D3 and sodium butyrate (NaB) at clinically achievable concentrations was synergistic for the inhibition of growth and stimulation of differentiation of a myeloid leukemia cell line.

Retinoic acid has been shown to inhibit the repair of the damage induced by radiation to cancer cells.

As used herein, "retinoid" refers to a molecule that binds and/or activates retinoic acid receptors or retinoid X receptors. The terms "retinoid" or "retinoids" include any suitable members of the generic class, including, but not limited to:

retinol (vitamin A); all-trans-retinol; vitamin A2 (3,4-didehydroretinol); 13-cis-retinol; 11-cis-retinol; 9-cis-retinol; 3,4-didehydro-retinol; 4-oxoretinol; 4-oxoretinaldehyde; retinyl esters; retinyl-glucuronides; all-trans-retinoic-acid (ATRA, Tretinoin, chemical name 3,7-Dimethyl-9-(2,6,6-trimethyl-1-cyclohexen-1-yl)-2,4,6,8-nonatetraenoic acid, CAS No. 302-79-4); 13-cis retinoic acid (Isotretinoin); 9-cis retinoic acid (9-cis-tretinoin); 4-hydroxy all-trans retinoic acid; N-(4-hydroxyphenyl) retinamide (Fenretinide); methyl retinoate; acetretin; alitretinoin (Panretin); bexarotene (Targretin); adapalene; etretinate; tazarotene; torularodin; retinaldehyde; 13-cis retinal; and phytanic acid. A wide variety of natural and synthetic RAR and RXR ligands are known and described in various publications and can be used as RAR or RXR agonists in the method of this invention.

Phenylacetic acid (PAA), phenylacetate (PA), phenylbutyric acid (PBA), phenylbutyrate (PB) and derivatives—PAA is naturally occurring in human plasma at micromolar concentrations. PAA and related aromatic fatty acids induce cytostatis, apoptosis and cell differentiation and promote maturation and reversal of malignancy of various human malignant cells. PAA is nontoxic and specifically inhibits the growth of tumor cells, while sparing normal tissues. Sodium phenylacetate (NaPA) and sodium phenylbutyrate (NaPB) have been used clinically. They are well tolerated and essentially free of adverse effects, even when administered in high doses over long periods.

Multiple mechanisms of drug action appear to be involved, and they include: activation of nuclear receptors, inhibition of mevalonic acid-pyrophosphate decarboxylase and the mevalonate pathway, inhibition of protein isoprenylation, regulation of gene expression, glutamine starvation, inhibition of histone deacetylation, induction of the peroxisome proliferator-activated receptor, alteration of the expression of genes implicated in tumor growth, invasion, angiogenesis and immunogenicity.

PAA is also able to enhance tumor responses to chemotherapeutic agents and radiation, while minimizing their adverse effects. Non-toxic amounts of PA, PB or other analogs increase the efficacy of radiation therapy and chemotherapy of some types of cancers. Many types of human cancer cells are sensitized to radiation upon in vitro exposure to PA or PB. Although they stimulate the proliferation of peroxisomes, which contain detoxifying glutathione S-transferase, PA and its analogs increase the sensitivity of cancer cells to cytotoxic agents. This effect is stronger in cells resistant to drugs or radiation than in cells already sensitive.

PA, PB and their derivatives can enhance immunosurveillance. Cancer cells employ many mechanisms to escape the surveillance of the immune system. For example, some tumors secrete immune suppressive factors that reduce the immune activity. Many cancer cells express very low levels of surface antigens that would allow the immune system to identify them. PAA can activate some dormant antigen genes, such as the cellular major histocompatibility antigens I and II (MHC Class I and II). PAA can also induce the expression of tumor antigens or viral proteins on the surface of cancer cells, which allows the adequate identification and elimination of these cells by the immune system.

Most PAA is conjugated to glutamine in the liver and kidney, and excreted in urine as phenylacetylglutamine (glutamine phenylacetate). PAA and its salts are effective in removing excess glutamine and excretion of waste nitrogen and are used in the treatment of hyperammonemia. Phenylbutyrate is a drug currently used in the treatment of urea cycle disorders. Glutamine is the major source of nitrogen for the synthesis of purines, pyrimidines and proteins, and is a source of energy in rapidly dividing cells. This amino acid is critical for the development and progression of cancer. Fast-growing cancer cells have an imbalanced glutamine metabolism, with accelerated utilization and catabolism and decreased synthesis of glutamine. Because the availability of glutamine is limiting, these cells are sensitive to further glutamine depletion. Glutamine antimetabolites and glutamine-depleting enzymes such as glutaminase have promising antineoplastic activities, but their clinical usefulness is limited by unacceptable toxicities. PAA has the ability to deplete the circulating glutamine, which may explain its antineoplastic activity.

PAA and its derivatives were clinically used in combination with lovastatin, for the treatment of malignant gliomas or other central nervous system tumors, in combination with RA for the treatment of neuroblastomas, in combination with hydroxyurea for the treatment of prostate cancer. PAA and its derivatives can induce malignant cell differentiation at relatively nontoxic doses and were used for the treatment of malignant melanomas and other neuroectodermal tumors and cancers involving medulloblastoma and astrocytoma-derived cells, for the treatment of glioblastomas and adenocarcinomas. Therapy of cancer with these compounds was not very successful. Studies indicated that administration of PB does not result in significant clinical responses in patients with solid tumors [11, 12]. Similarly, no complete or partial responses were observed in patients with myelodysplastic syndromes and acute myeloid leukemia [13].

Phenylacetic acid derivatives include, without limitation: phenylacetic acid, phenylpropionic acid, phenylbutyric acid, 1-naphthylacetic acid, naphthyl acetate, phenoxyacetic acid, phenoxypropionic acid, phenoxybutyric acid, 4-chlorophenylacetic acid, 4-chlorophenylbutyric acid, 4-iodophenylacetic acid, 4-iodophenylbutyric acid, α-methylphenylacetic acid, α-methoxyphenylacetic acid, α-ethylphenylacetic acid, α-hydroxyphenylacetic acid, 4-fluorophenylacetic acid, 4-fluorophenylbutyric acid, 2-methylphenylacetic acid, 3-methylphenylacetic acid, 4-methylphenylacetic acid, 3-chlorophenylacetic acid, 3-chlorophenylbutyric acid, 2-chlorophenylacetic acid, 2-chlorophenylbutyric acid, 2,6-dichlorophenylacetic acid, and the salts of these compounds.

Vitamin D is a family of fat-soluble prohormones that have essential functions in the regulation of growth, differentiation, maturation and function of cells. They participate in many biological activities: regulation of gene transcription, regulation of serum calcium, regulation of phosphorus homeostasis, modulation and stimulation of the immune system, modulation of insulin secretion by pancreatic B cells, regulation of the parathyroid gland, muscle cell function, osteogenesis, promotion of collagen synthesis, etc. [14].

Vitamin D and its analogs are potent inducers of differentiation and inhibitors of proliferation of normal and malignant cells. Calcitriol (1α,25-dihydroxyvitamin D3) was shown to be anti-proliferative and pro-differentiative in numerous malignant cells: breast, ovaries, colon, brain, prostate, hematopoietic. Calcitriol and other vitamin D3 analogs are effective in the treatment of hyperproliferative diseases, metabolic diseases and diseases of abnormal cell differentiation (cancer, psoriasis). They are useful in the treatment of many forms of cancer, such as skin cancer, prostate cancer and colon cancer.

The effect of calcitriol is mediated through the steroid hormone nuclear vitamin D3 receptor (VDR). Nuclear receptors specific for active vitamin D compounds are present in normal cells, as well as many neoplastic cells: prostate carcinoma cells, carcinomas of the breast and colon.

Calcitriol has an antiangiogenic effect. It significantly inhibits endothelial cell proliferation induced by vascular endothelial growth factor (VEGF). Calcitriol induces the regression of sprouting of elongated endothelial cells by causing apoptosis within the cell population.

Vitamin D3 and its analogs interact synergistically with other inducers of differentiation, such as retinoids, phorbol 12-myristate 13-acetate (PMA) and bryostatin-1. The vitamin D and retinoid or rexinoid nuclear receptors (RAR and RXR) are members of the same family of receptors. The signaling pathways of these and other nuclear receptors are linked. The vitamin D receptors form heterodimers with RAR and RXR that have biological significance. Cooperation between these two receptor pathways might explain why the receptor ligands have similar and sometimes synergistic effects in biological systems. Co-stimulation of VDR-RXR or VDR-RAR heterodimers with both vitamin D and retinoids has been the basis for combination therapies. The synergistic activity of vitamin D analogs and retinoids in inhibiting cellular growth and promoting differentiation is evident in many cell lines. Synergistic effects are also seen in vivo for the anti-tumor activities of these families of compounds. Mechanistically, these combinations have a synergistic effect for induction of apoptosis and inhibition of angiogenesis. Tumor-induced angiogenesis is synergistically inhibited when calcitriol is combined with ATRA, 9-cis retinoic acid, and 13-cis retinoic acid in mice transplanted with transformed human keratinocytes [15].

As in the case of other differentiation inducers, active vitamin D compounds can enhance the anti-tumor efficacy of cytotoxic drugs. Calcitriol and other vitamin D derivatives act synergistically and potentiate the activity of cytotoxic agents, such as cisplatin, carboplatin, paclitaxel and docetaxel.

The association of dexamethasone with calcitriol potentiates the anti-tumor effect and reduces the hypercalcemia induced by the vitamin D3 derivative [16].

Calcitriol was also found to be synergistic with ionizing radiation (IR) and potentiate IR-induced apoptosis. A calcitriol analog produced additive growth inhibition and apoptosis when combined with IR on MCF-7 breast cancer cells.

There are reports of beneficial effects of the association of vitamin D analogs and retinoids in the treatment of some forms of cancer in human patients. Unfortunately for cancer patients, the synergistic effects are not always observed and are not of great significance. The administration of vitamin D compounds or derivatives together with other pharmaceutical agents, such as cytotoxic agents, was not very effective in the treatment of hyperproliferative diseases.

The overall epidemiologic data about the correlation between vitamin D or calcitriol levels and prostate cancer is mixed. Most epidemiological studies have shown no correlation between calcitriol levels and risk of prostate cancer. One study found that low calcitriol level is an important predictor of risk for prostate cancer in men over 57 years old. Another study reached a different conclusion: men younger than 52 with low 25-hydroxy-vitamin D3 levels had a more than threefold higher risk of developing prostate cancer than those with higher levels, but the risk of prostate cancer due to low 25-hydroxy-vitamin D3 levels disappeared in those men older than 52. Daily calcitriol was tested in both hormone-naïve and androgen-independent prostate cancer with no significant effect. In hormone-naïve patients, calcitriol had a small effect on prostate-specific antigen (PSA) levels, possibly because of its cytostatic effect on prostate cancer cells. Calcitriol can also slow the rate of rise of PSA in patients with advanced prostate cancer.

There is good epidemiologic evidence indicating that high levels of vitamin D contribute to lower rates of colorectal cancer [17].

The clinical use of calcitriol and other vitamin D3 analogs is severely limited by the increase of calcium levels in blood and urine. Calcitriol can only be administered in small doses before hypercalcemia and/or hypercalcuria develop. The concentration of calcitriol achieved in normal volunteers and patients is only modestly above the physiologic range. Calcitriol concentrations that, based on preclinical data, are thought to be necessary for antineoplastic activity are not achievable with conventional daily dosing.

Daily calcitriol also had little activity in patients with myelodysplastic syndrome and ovarian cancer. Combined with isotretinoin, calcitriol was found to be inactive in patients with ovarian cancer. Pilot studies have also examined daily calcitriol in combination with cytarabine and with cytarabine and hydroxyurea in the treatment of myeloid and lymphoid leukemia. While some activity was seen with these combinations, the studies were not designed to isolate the effect of calcitriol. The combination of cytarabine with 13-cis retinoic acid and calcitriol in myelodysplastic syndrome was not more effective than cytarabine alone.

Analogs of vitamin D3 have been developed that retain the antiproliferative activity but lack or substantially eliminate the hypercalcemic side effects. Some of these analogs have stronger antitumor and antiproliferative effects than calcitriol and are more potent than calcitriol in inhibiting neoplastic growth.

The term "vitamin D analog" is defined as a compound capable of binding a vitamin D receptor (not necessarily all) or being converted in vivo into a compound capable of binding a vitamin D receptor (not necessarily all). The term "vitamin D analog" includes, but is not limited to: vitamin D2 (ergocalciferol), vitamin D3 (cholecalciferol), and their derivatives, such as calcifediol; calcitriol; calcipotriol; ergosterol; ergocalciferol; dihydrotachysterol; 1,25-dihydroxyergocalciferol; 25-hydroxydihydrotachysterol; 22-oxa-vitamin D3; 1,25-dihydroxychloecalciferol; vitamin D3 (1α,25-dihydroxy-20-epi-vitamin D3); 19-nor vitamin D3; and 1α,25-dihydroxy-20-epi-vitamin D3. The active form of vitamin D and its natural metabolite is 1α,25-dihydroxyvitamin D3, also known as calcitriol.

Glucocorticoids exert a broad variety of effects, mediated by both genomic and non-genomic mechanisms. Genomic mechanisms are induced at low concentrations and have a slow onset, due to the time required for changes in gene expression. At higher concentrations, corticosteroids can also act through non-genomic mechanisms.

Anti-inflammatory agents are not traditionally used in cancer treatment, as they suppress the immune system. The combination of glucocorticoids and cytotoxic agents has been suggested to be avoided. In cancer therapy, steroids are used to control the symptoms and inflammation that surround the tumor lesions. Corticosteroids inhibit the production of tumor necrosis factor and thus reduce all the negative effects associated with it, such as malaise or loss of appetite. Corticosteroids have suppressing activity on cells of lymphatic origin and are used by themselves or in combinations with classical chemotherapeutic agents in the treatment of lymphatic cancers (e.g. chronic and acute lymphatic leukemia, Hodgkin's and non-Hodgkin's lymphomas) and some hematological malignancies (multiple myeloma). Corticosteroids also help maintain high levels of blood glucose, which is useful for brain tumors.

Some corticosteroids have the ability to inhibit mitotic division and stop DNA synthesis. Glucocorticoids have angiostatic effects and can decelerate solid tumor growth by interfering with tumor vascularization. Cortisone inhibits tumor angiogenesis in mice and the addition of cortisone to chemotherapy enhances antitumor efficacy without increasing toxicity. There is a class of steroids named "angiostatic steroids" that have no glucocorticoid or mineralcorticoid activity, but have antiangiogenic activity. These angiostatic steroids can be synthetic or natural, with the synthetic steroids having greater antiangiogenic activity. Among the natural angiostatic steroids, tetrahydrocortisol, a natural metabolite of cortisone, is one of the most potent. The combination of angiostatic steroids administered with heparin fragments that lack anticoagulant activity has a strong antiangiogenic effect. Glucocorticoids are rapidly cleared from circulation and accumulate at tumor sites only to a very limited extent.

Glucocorticoids potentiate the anti-tumor effect of calcitriol and decrease the calcitriol-induced hypercalcemia. Dexamethasone enhances the growth inhibition of tumor-derived endothelial cells mediated by calcitriol and potentiates the antitumor effects of calcitriol in vitro and in vivo. In combination with calcitriol, dexamethasone induces a significant time- and dose-dependent increase in VDR expression and an enhanced apoptotic response, as compared to calcitriol alone.

Corticosteroid drugs include, but are not limited to: prednisone, methylprednisone, dexamethasone, betamethasone, prednisolone, methylprednisolone, triamcinolone, cortisone, hydrocortisone, fludrocortisone, budenoside, fluocortolone and tetrahydrocortisol.

There are over 600 natural carotenoids, and many of them have pro-vitamin A activity. Humans cannot synthesize carotenoids de novo and must obtain them from diet. The carotenoids are fat-soluble antioxidants that quench reactive oxygen species and scavenge free radicals. Independent of their antioxidant activity or the potential for conversion to retinoids, carotenoids have cancer preventive properties. They are effective inhibitors of the growth of cancer cells. Some carotenoids, such as astaxanthin, can stimulate the immune system by enhancing cell-mediated and humoral immune response. They suppress the production of inflammatory cytokines Many carotenoids, such as capsanthin, capsorubin, lycopene, lutein, antheraxanthin and violaxanthin, inhibit the function of multidrug resistance (MDR) proteins. Carotenoids are drug resistance modifiers and are able to induce apoptosis in cancer cells, which makes them excellent adjuvants to antineoplastic drugs [18]. The carotenoids have a synergistic effect with each other.

$\beta$-carotene is a lipid-based, pro-vitamin A antioxidant that is very effective in protecting lipids against peroxidation. In mammals, $\beta$-carotene can undergo oxidative cleavage at the central double bond to give two equivalents of the aldehyde retinal, which upon reduction yields retinol (vitamin A). In addition to protection against oxidation and conversion to vitamin A, $\beta$-carotene's anticancer effects are mediated through other mechanisms, such as inhibition of cell proliferation, induction of detoxifying enzymes, and up-regulation of intercellular communication across the gap junction.

$\beta$-carotene is safe in humans even when administered in large doses over long periods. It did not show any toxicity in patients who took 180-300 mg $\beta$-carotene/day over 10 years. The epidemiological studies of the effect of $\beta$-carotene on cancer prevention are contradictory, with many studies indicating a negative or lack of effect in many types of cancers.

The natural form of $\beta$-carotene has been shown to be more active than the synthetic $\beta$-carotene. For example, natural $\beta$-carotene protects against radiation-induced transformation in vitro, whereas synthetic $\beta$-carotene was ineffective. $\alpha$-carotene is a more potent inhibitor of cancer cell growth than $\beta$-carotene.

Lycopenes are unsaturated, non-provitamin A carotenoids. Lycopenes concentrate in specific parts of the body, including the breast, prostate and pancreas. Lycopene is among the most efficient singlet-oxygen quenchers of all natural carotenoids. Lycopene has been shown to inhibit proliferation in various cancer cell lines, and epidemiological studies have shown an inverse correlation between lycopene plasma levels and prostate cancer. Lycopene supplementation has positive effects on patients with localized prostate cancer. Men with elevated levels of plasma lycopene have a lower risk of developing prostate cancer. For men with low lycopene, $\beta$-carotene supplements were associated with risk reductions comparable to those observed with high lycopene.

The mechanisms by which lycopene induces its anticancer effects are not completely clear. It is possible that it induces the differentiation of prostate cancer cells or it inhibits the oxidation of cholesterol, which affects the synthesis and metabolism of steroid hormones. The antiproliferative activity of lycopene is even more evident when it is associated with $\alpha$-tocopherol.

The term "carotenoid" include any suitable members of the generic class, including but not limited to $\beta$-carotene, $\alpha$-carotene, lycopene, lutein, capsanthin, capsorubin, cryptoxanthine, antheraxanthin, canthaxanthin, violaxanthin, zeaxanthin, apo-carotenal, xanthophylls, procarotenoids and derivatives thereof.

Cytotoxic phenolic compounds. Without limitation, the cytotoxic phenolic compounds that can be used in the combination therapy of this invention include vitamin K, L-3,4-dihydrophenylalanine, hydroquinone, metol, coenzyme Q (Q10), 4-hydroxyanisole, butylated hydroxyanisole, dopamine, catecholamines, tertbutylcatechol, resorcinol, 6-hydroxydopa and methyl gallate. The most abundant catecholamines are epinephrine (adrenaline), norepinephrine (noradrenaline) and dopamine.

Vitamin K is a quinone cofactor involved in hemostasis and blood coagulation. Quinones have the ability to induce oxidative stress through redox cycling. 1,4-Naphthoquinones have antitumor effects through multiple mechanisms. They are potent inhibitors of human cancer cell growth and angiogenesis. Vitamins K2 and K3 have been shown to inhibit angiogenesis in a variety of models. Vitamins K2, K3 and K5 were shown to induce apoptosis in different types of cancer cells: leukemia cells, gastric cancer cell lines and colorectal cancer cells. Geranylgeraniol, a polyprenylalcohol composing the side chain of vitamin K2, is a potent inducer of apoptosis in cancer cell lines. Vitamin K2 (menaquinones, MK3, MK4, MK5) and geranylfarnesol have apoptosis-inducing activity in vitro for freshly isolated leukemia cells and for leukemia cell lines, while vitamin K1 has no effect.

Many studies have shown specific clinical benefits of MK4 at pharmacological doses for osteoporosis and cancer, although the mechanisms are poorly understood. Vitamin K2 (menaquinone) has anti-cancer effect in particular for hepatic cancer. Women with viral liver cirrhosis receiving a daily supplement of 45 mg vitamin K2 (menaquinone) for a period of two years were nearly 90% less likely to develop liver cancer. Epidemiologic studies found an inverse association between the intake of menaquinones, but not that of phylloquinone, and prostate cancer. Menadione (vitamin K3) lowers intracellular pools of reduced glutathione and was combined with mitomycin C in an attempt to overcome thiol-mediated resistance to alkylating-agent chemotherapy. Preclinical evidence indicates that menadione enhances the cytotoxicity of mitomycin C, but the combination therapy of menadione and mitomycin C was ineffective in a phase II clinical trial of advanced gastrointestinal cancers.

Retinoids and vitamin K2 function synergistically to inhibit growth of human hepatocellular carcinoma cells. The combination of MK5 plus ATRA resulted in enhanced induction of apoptosis as compared to each reagent alone. Vitamin K does not impair the growth inhibiting effect of coumarins and is able to offset the anticoagulant effect of coumarins without adversely affecting their anticancer activity.

"Vitamin K" means any member of the vitamin K group, a group of naphthoquinone derivatives. The most common vitamin K members include, but are not limited to: phylloquinone (vitamin K1), menaquinones (vitamin K2, menaquinone 3, 4, and 5), menadione (vitamin K3), vitamin K4, K5, and the like. "Vitamin K" also means any derivatives and analogs of the vitamin K group members with similar biological functions, including but not limited to dihydrovitamin K and derivatives and analogs thereof.

Levodopa (L-3,4-dihydroxyphenylalanine, Madopar), dopamine and related compounds have significant antitumor activity in several experimental systems. The active agents seem to be the quinones obtained through the oxidation of quinols by tyrosinase. The quinones are able to inhibit DNA synthesis, are potent oxidizing agents and inactivate enzymes that are sensitive to oxidation. The quinols have a higher inhibition activity on cells that possess oxidative enzymes (e.g. tyrosinase). The only human cells known to contain the enzyme tyrosinase are the melanocytes. Pigmented melanoma cells have a high tyrosinase activity and were shown to be very sensitive to quinols. Neuroblastoma and leukemia cells are also sensitive to quinols, but the mechanism of action is less clear. It is possible that the tumor selectivity of these quinols is the result of the ability of these compounds to be oxidized by tyrosinase (present in high levels in melanoma cells) and the relative inability of tumor cells to decompose the radical oxides formed as a consequence of the oxidation.

Lipotropes are dietary methyl donors and cofactors involved in one-carbon metabolism. They are important for methylation of genomic DNA and synthesis of nucleic acid. They include: methionine, choline, folate, vitamin B12 (cobalamin), vitamin B6 (pyridoxine) and vitamin B2 (riboflavin). Maintenance of normal methionine metabolism, promoted by supplementation with methionine or cysteine, with folic acid, choline or betaine, may avoid aberrant methylation that can result in DNA damage and mutations.

In vitro, lipotrope supplementation inhibits the growth of human breast cancer cell lines and significantly increases the percentage of apoptotic cells. Human epidemiological studies are contradictory: some found no correlation between lipotrope intakes and the risk of cancer, while one study found that consumption of choline was associated with a lower risk of breast cancer, when comparing the highest and the lowest quintiles.

Dipyridamole is a platelet inhibitor, generally used to prevent blood clot formation. Dipyridamole is also an inhibitor of the transport of various molecules across cell membranes. Dipyridamole inhibits nucleoside transport and hence the salvage pathways for the biosynthesis of precursors of DNA synthesis and repair.

The nucleotides that cells need for DNA synthesis are obtained either by de novo synthesis or by salvage and reuse. Many antimetabolites block the de novo synthesis of nucleotide precursors, which are eventually converted into the DNA building blocks. The cell can compensate for the inhibition of synthesis of fresh nucleosides by increasing their uptake from outside sources. Dipyridamole and other transport inhibitors block nucleosides from entering the cells and prevent their use in DNA synthesis. Inhibitors of nucleoside transport block the salvage of extracellular nucleosides and potentiate the antiproliferative effect of de novo inhibitors of DNA synthesis. By inhibiting all pathways that can supply essential nucleosides, synthesis of DNA and RNA is prevented and cells cannot proliferate. Inhibition of both de novo and transport or salvage pathways has a synergistic antiproliferative effect.

The nucleoside salvage pathway was found to contribute to resistance of cancer cell lines to the antimetabolite methotrexate. This pathway could be blocked by the nucleoside transport inhibitor dipyridamole. Dipyridamole can also bind to P-glycoprotein and potentially reverse multidrug resistance in vitro (it is a multidrug-resistance-modulating agent). Clinically achievable concentrations of dipyridamole enhance sensitivity to several drugs in patient-derived leukemia cells.

Unfortunately, in vivo application of dipyridamole is hampered by its high protein-binding, which prevents the inhibition of nucleotide transport by dipyridamole. Clinically, dipyridamole showed little or no significant improvement in patient response. The addition of oral dipyridamole does not appear to improve the efficacy of the standard leucovorin/fluorouracil regimen in patients with advanced colorectal cancer. An increase in 5-FU dose-intensity was observed for the fluorouracil/folinic acid/dipyridamole combination, but it was not clinically relevant.

Without limitation, the nucleoside transport inhibitors include compounds such as dipyridamole, dilazep and nitrobenzylthioinosine.

Vitamin C (ascorbic acid) is an excellent hydrophilic antioxidant. It can scavenge radicals, such as singlet oxygen and hydroxy radicals. Vitamin C strengthens the immune system. It stimulates the production of T4 killer cells and white blood cells. Vitamin C reduces platelet aggregation. It provides antioxidant protection for folate and vitamin E. Vitamin C has a short half-life in the body.

Forms of vitamin C suitable for use in the combination therapy of this invention include ascorbic acid, ascorbic acid salts (calcium, zinc, magnesium, sodium ascorbate), ascorbic acid esters, ascorbyl palmitate, sodium ascorbyl phosphate, nicotinamide ascorbate, isoascorbic acid and ascorbigen. Mixtures of ascorbate complexes can also be used, as they have different half-lives and different affinities for the collagen matrix. The term "vitamin C" as used herein includes derivatives that have biological vitamin C activity, e.g. esters and salts.

7-hydroxycoumarin (umbelliferone) is a natural coumarin derivative. In humans, 7-hydroxycoumarin (7-HC) is the major metabolic product of coumarin. Coumarins have multiple biological activities and broad pharmacological properties, including: immuno-modulating effects, stimulation of the immune system, stimulation of macrophages and other cells of the immune system, antiviral and antimicrobial activity, scavenging of reactive oxygen species, inhibition of lipid peroxidation and superoxide generation, anti-coagulant and anti-inflammatory effects, inhibition of the biosynthetic conversion of arachidonic acid to prostaglandins, etc. Coumarins are considered to be biological response modifiers.

Coumarins have complex anticancer properties. Coumarins have been tested by themselves or in combinations for the treatment of various cancers. Coumarin and its metabolite, 7-HC, are non-toxic and can inhibit the growth of several malignant cell lines. 7-HC has fewer side effects and greater cytostatic activity than coumarin. Warfarin inhibits tumor spread and stimulates granulocytes, lymphocytes and macrophages. While not wishing to be bound by any theories, it is believed that the anticancer activities of coumarins are mediated through multiple mechanisms: coumarins cause significant changes in cell growth and differentiation of sensitive cancer cells, modulate microtubule disassembly, modulate multidrug resistance transporters, inhibit quinone reductases and inhibit the activation of nuclear factor-κB in tumor cells. Modulation of microtubules is a mechanism exploited by other known anticancer compounds, such as taxols.

Coumarins prevent the carcinogenicity of carcinogens, enhance the efficacy of chemotherapy, prevent the development of multidrug resistance to chemotherapeutics, and have radiosensitizing properties. Because of their radiosensitization and chemopotentiation activities, coumarins can be employed in combination with ionizing radiation and/or chemotherapy. Coumarins can be used to treat the side effects caused by radiotherapy. The coumarin/troxerutine combination was able to protect the salivary glands and mucosa against radiogenic sialadentis and mucositis in patients undergoing radiotherapy for head and neck cancer.

Without limitation, coumarins that can be used in the methods of the present invention include 7-hydroxycoumarin, coumarin, 4-hydroxycoumarin, esculetin (6,7-dihydroxycoumarin), warfarin and their prodrugs, metabolites or derivatives.

Flavonoids: rutin (also called rutoside, quercetin-3-rutinoside and sophorin) is a glycoside of the flavonoid quercetin. Flavonoids are strong antioxidants found and extracted from plants. They can be in a glycosylated form or non-glycosylated form, esterified with aliphatic or aromatic acids. Flavonoids have the ability to scavenge and annihilate free radicals, and quench singlet oxygen species. Flavonoids prevent the degradation of ascorbic acid and are involved in the restitution of vitamin E.

Flavonoids have an extraordinary range of pharmacological properties in humans, including anticancer properties. When used as adjuvants to cancer therapy, flavonoids affect both cancer cells and normal tissue. They increase the efficacy of cancer therapies and substantially reduce the toxic side effects of cytotoxic drugs and radiation. Flavonoids enhance the sensitivity of cancer cells to anti-cancer agents, drugs or radiation. They reduce the development of multidrug resistance in cancer cells and sometimes restore sensitivity to the cancer cells that are resistant. Flavonoids protect non-cancer cells and tissue against the damages induced by cytotoxic agents. They increase protein biosynthesis in healthy, normal cells, but not in cancer cells, thus promoting the regeneration of healthy tissue without supporting the proliferation of cancer cells. Rutin is a potent VEGF inhibitor (angiogenesis inhibitor).

Flavonoids show anticancer effect synergistic with other agents: vitamin C, retinoids, tamoxifen and tocotrienols. Quercetin, a flavonoid that is almost ubiquitous in plants, has synergistic activity with the agents commonly used in chemotherapy. Flavonoids prevent or reduce the export of chemotherapeutic agents out of a cell.

Silymarin is isolated from the seed, fruit or berries of milk thistle (Silybum eburneum Coss. & Dur. or Silybum marianum (L.) Gaertner). Silymarin is a complex mixture of polyphenolic molecules, including some closely related flavonolignans (silybin A, silybin B, isosilybin A, isosilybin B, isosilybinin, dehydrosilybin, silychristin, isosilychristin, silydianin) and the flavonoid taxifolin. Silibinin, the major component of silymarin (approximately 80%), is primarily a mixture of 2 diasteroisomers, silybin A and silybin B, in a roughly 1:1 ratio. Silibinin has the major biological activity, while the other compounds in silymarin have less physiological activity: isosilybinin occurs in very small amounts, silydianin is extensively metabolized, and silycristin is poorly absorbed by the gastrointestinal tract.

Silymarin has remarkable antioxidant and antiradicalic properties. It is able to reduce or prevent lipid peroxidation and membrane destruction in cells. It has antimutagenic activity, both for spontaneous mutagenesis or mutagenesis induced by radiation and chemicals.

Silymarin has an enterohepatic circulation. After oral administration, silymarin is absorbed by the intestinal tract and transported to the liver, where it is taken up by hepatocytes and primarily excreted into bile. A relatively small amount of silymarin is excreted by kidneys, but most of it is released together with the bile back in the intestine where it is reabsorbed. This enterohepatic circulation is believed to account for silymarin's affinity for the liver and its lack of antioxidant activity in other organs, such as the lungs, kidneys or spleen.

Silymarin stabilizes hepatic cell membrane to inhibit the intracellular influx of noxious substances and accelerates protein biosynthesis of hepatic cells, resulting in the stimulation of the regeneration of hepatic cells and restoration of liver functions. Silymarin has anti-hepatotoxic activity and provides a protective effect to the liver from damage by toxins. Silymarin has been used for the treatment of liver diseases, chronic inflammatory liver diseases, cholecystic disease, jaundice, toxic liver damage (induced by alcohol, drugs, or environmental toxins), hepatitis, cirrhosis and Amanita mushroom poisoning. Silymarin can be used in adjuvant cancer therapy, as it is able to reduce the toxicity of antineoplastic drugs, such as cisplatinum and anthracyclines.

Silymarin has affinity for estrogen receptors and it accumulates at sites and organs that over-express the receptors, where it performs its antioxidant, anti-inflammatory and anti-proliferative effects. Silymarin blocks nuclear translocation and inhibits activation of androgen receptors, thus reducing the transactivation of specific genes controlled by this receptor. The silymarin flavonoids have affinity for estrogen receptors type II and a marked antiproliferative activity on uterus, ovary and breast tumor cell lines resistant to cisplatin and adriamycin. In vitro, silymarin can inhibit the proliferation of independent-androgenic prostate cancer cells. Silibinin in complex with phospholipids inhibits the proliferation of hormone-dependent tumors of the ovary and breast, and has synergic effects with platinum complexes. Numerous studies on silymarin and milk thistle extracts have shown them to be virtually without side effects when used in therapeutic doses.

The term "silymarin" disclosed herein can be prepared by extracting the fruit or seed of all the silymarin containing plants that belong to the Compositae family, such as dandelion, wild thistle (Silybum marianum) and the like, or being purchased from conventional companies, such as Sigma Co. (USA). Where reference is made to silymarin, it can be replaced by one or more of its constituents.

Vitamin E is a hydrophobic vitamin antioxidant. Vitamin E is the general name for a family of compounds broadly consisting of tocopherols and tocotrienols. α-tocopherol is the most abundant and biologically active form of vitamin E. α-tocopheryl succinate (α-TS) was found to be the most active form of vitamin E in vitro and in vivo for inhibition of proliferation, induction of differentiation and apoptosis of cancer cells without affecting the proliferation of most normal cells [19]. Studies in breast and prostate cancer cells have shown that the dl-α-tocopherol isomer decreases proliferation and induces apoptosis. Studies of thymidine incorporation have shown that vitamin E supplementation reduces DNA synthesis and causes fragmentation, leading to apoptosis and inhibiting cancer cell growth in a dose-dependent fashion. Cells vary in sensitivity to this effect, with breast and prostate cancer cells being most sensitive.

α-TS enhances the growth-inhibitory effects of ionizing radiation, chemotherapeutic agents, and some biological response modifiers on cancer cells, but not on normal cells. γ-tocopherol has a greater cell inhibitory activity in vitro and at lower concentrations than synthetic α-tocopherol.

Vitamin E is present in cell membranes, where it is essential for the protection of the phospholipid membrane against lipid peroxidation and oxidative stress. Tocopherols scavenge free radicals and inhibit the oxidation of unsaturated fatty acids by trapping peroxyl free radicals. In addition to antioxidant properties, other mechanisms may also be responsible for the anti-proliferative activity of vitamin E. α-TS alters the expression of genes involved in differentiation, proliferation and apoptosis.

Vitamin E can inhibit the growth of normal smooth muscle cells and certain human cancer cell lines. It can induce a variety of effects in cancer cells: differentiation, apoptosis, inhibition of proliferation. The type of effect depends on the vitamin E compound, type of cancer cell, culture conditions, duration and concentration of treatment. Generally, lower concentrations induce differentiation and higher concentrations induce apoptosis of cancer cells.

Besides the anticancer activity, vitamin E also has other beneficial effects. It is an immune stimulant that has anti-inflammatory effects, protects the nervous system, protects against cardiovascular disease, lowers cholesterol and raises high-density lipoprotein. Vitamin E regulates the proliferation and repair of the cells that line the arteries, and prevents the formation of blood clots on artery wall (antiatherogenic effect). There is an inverse relationship between the plasma levels of vitamin E and the incidence of heart disease. Increased intake of vitamin E is associated with reduced risk of coronary heart disease in certain high-risk groups.

Vitamin E is synergistic with selenium and helps protect vitamin A from degradation. In the absence of other antioxidants to protect it (vitamin C, flavonoids), vitamin E can be harmful (for example, it can accelerate the oxidation of low-density lipoprotein).

Together with dietary micronutrients, vitamin E can be used as an adjunct to cancer therapies in order to improve their efficacy. Epidemiological and clinical studies indicate that there is an inverse relationship between vitamin E consumption and the overall cancer morbidity and mortality. The Alpha-Tocopherol, Beta-Carotene (ATBC) Cancer Prevention Study, a randomized trial conducted in more than 29,000 male smokers in Finland, showed that out of the 246 new cases of prostate cancer identified during the 5 to 8-year intervention period, only 99 cases occurred among participants who received 50 mg of vitamin E daily, compared with 147 cases among those who did not receive vitamin E, a striking one-third reduction [20]. The men in the highest quintile of baseline serum concentrations of α-tocopherol had significantly lower risks of total and cause-specific mortality, including cardiovascular disease and cancer, than did the men in the lowest quintile of baseline serum concentrations of α-tocopherol. The men with higher serum concentrations of vitamin E had significant reductions in mortality due to lung or prostate cancer, ischemic or hemorrhagic stroke, and respiratory disease.

The HOPE (Heart Outcomes Prevention Evaluation) trial of 7,000 patients randomized to 400 IU/day vitamin E versus placebo for an average of 7 years showed no effect on cancer incidence or cardiovascular events. In a large, long-term trial of male physicians, supplementation with 400 IU of vitamin E every other day and 500 mg of vitamin C daily did not reduce the risk of prostate or total cancer.

In a large cohort study (VITAL), a higher intake of vitamin E reduced the risk of advanced prostate cancer. A prospective analysis of data from 29,361 men in the screening arm of the Prostate, Lung, Colorectal, and Ovarian (PLCO) Cancer Screening Trial, found no overall associations between intakes of dietary or supplemental vitamin E and prostate cancer risk. However, among men who were current smokers or who had quit smoking within the past 10 years, those with supplemental vitamin E intakes greater than 400 IU/day had a statistically significant 71% reduction in risk of advanced prostate cancer compared with those who did not take supplemental vitamin E.

The CPS-II clinical trial evaluated the impact of vitamin E on bladder cancer mortality [21]. After adjusting for variables, including patient sex, age, vegetable intake and smoking, only patients receiving vitamin E supplements for at least 10 years demonstrated a decreased risk of death from bladder cancer. Long-term supplementation with α-tocopherol substantially reduced prostate cancer incidence and mortality in male smokers.

Diets high in vitamin E are associated with a lower risk of cancer. It is possible that vitamin E also stimulates immunologic function.

Vitamin E is available in various forms. The term "vitamin E" as used herein refers to natural vitamin E, as well as derivatives thereof which have biological vitamin E activity. It includes (a) tocopherols: alpha, beta, gamma, delta tocopherol (chemical names (2R)-2,5,7,8-Tetramethyl-2-[(4R,8R)-(4,8,12-trimethyltridecyl)]-6-chromanol; (2R)-2,5,8-Trimethyl-2-[(4R,8R)-(4,8,12-trimethyltridecyl)]-3,4-dihydrochromen-6-ol; (2R)-2,7,8-Trimethyl-2-[(4R,8R)-4,8,12-trimethyltridecyl]-6-chromanol; and (2R)-2,8-Dimethyl-2-[(4R,8R)-4,8,12-trimethyltridecyl]-6-chromanol), d-α-tocopherol (the natural form of vitamin E), water-soluble vitamin E, d-tocopherols, l-tocopherols, racemic dl-α-tocopherols (synthetic), mixed tocopherols; (b) esters, such as tocopheryl acetate, propionate, butyrate, nicotinate, succinate, hemisuccinate, and others; (c) tocotrienols (also a form of vitamin E that correspond to the tocopherols, but with unsaturated side chain), such as α-tocotrienol, β-tocotrienol, γ-tocotrienol, δ-tocotrienol, d-tocotrienols, l-tocotrienols, dl-tocotrienols.

Isoprenoids can modulate cell growth, induce cell cycle arrest, suppress cellular signaling and initiate apoptosis and differentiation. Isoprenoids, such as farnesol (an acyclic sesquiterpene), farnesyl homologs, γ-tocotrienol and various farnesyl derivatives, downregulate the activity and post-translational modification of 3-hydroxy-3-methylglutaryl coenzyme A (HMG CoA) reductase. They inhibit the reductase synthesis and accelerate its degradation. The same effect on HMG CoA reductase was seen for cyclic monoterpenes, d-limonene, menthol, perillyl alcohol and β-ionone, a carotenoid fragment. HMG CoA reductase activity in tumors is elevated and resistant to sterol feedback regulation. The combination of γ-tocotrienol, a potent isoprenoid, and statins, such as lovastatin, which are HMG CoA reductase inhibitors, attenuate the reductase activity in tumors. The combination has a synergistic effect on the growth of human DU145 and LNCaP prostate carcinoma cell lines.

Selenium is a nutrient vital to human health. Selenium is an essential constituent of seleno-proteins, such as glutathione peroxidases, thioredoxin reductase, iodothyronine 5'-deiodinases and others. Selenium has anticarcinogenic and cancer therapeutic effects that are achieved through multiple mechanisms. Along to vitamin E, selenium is a component of glutathione peroxidase, an antioxidant enzyme critical in the control of oxygen metabolism. Glutathione peroxidase catalyzes the breakdown of hydrogen peroxide, prevents the generation of free radicals and protects DNA, cells and tissue from damage by oxygen radicals, such as those produced by cytotoxic agents and radiation. Selenium is a vascular stimulant that improves immunity and increases T-cell levels (enhances the clonal expansion of activated T-cells). The antitumorigenic effect of selenium is also due to its metabolites. Selenium has antimutagenic effects. It prevents the activation and promotes the inactivation of oncogenes. It prevents cell malignization and induces partial retransformation of tumor cells. Selenium increases the absorption of vitamin E by the body and the combination of selenium and tocopherols has a synergistic anticarcinogenic effect. Co-administration with zinc increases selenium retention in certain organs. The anticancer effect of selenium may relate to its ability to enhance the immune response or to its ability to produce anti-tumorigenic metabolites (e.g., methyl selenol or its precursors) that can perturb cancer cell metabolism, inhibit angiogenesis, and induce apoptosis of cancer cells.

Selenium protects against chemotherapy toxicity and potentiates the antitumor activity of chemotherapeutic agents. Sodium selenite alleviates the side-effects and immunosuppressive effects of cytotoxic chemotherapeutic agents. When associated with anticancer agents, selenium prevents the induction of resistance to melphalan or cisplatin and enhances the chemotherapeutic effect of taxol and doxorubicin beyond that seen with the chemotherapeutic drugs alone. Selenite potentiates the cytotoxicity of 5-FU, oxaliplatin, and irinotecan in some cancer cells.

In humans, oral selenium is selectively taken up by the prostate, and selenium administration reduces the incidence of prostate cancer. Geographical correlation studies suggest an inverse relationship between selenium status and cancer incidence. Clinical studies indicate that daily supplementation with selenium cuts the overall risk of cancer. Supplementation with 200 μg selenium per day has considerable immunoenhancing effects: 118% increase in cytotoxic-lymphocyte-mediated tumor cytotoxicity, 82% increase in natural-killer-cell activity. Selenium deficiency is linked to the occurrence, virulence, or disease progression of some viral infections.

Without limitation, the selenium derivatives that can be used in the combination therapy of this invention include a chemical or composition containing the element selenium, such as selenomethionine, seleno-L-methionine, selenocysteine, methylselenocysteine, selenized yeast (Se-rich yeast, yeast-derived selenium that contains a cocktail of selenium in a variety of chemical forms), Se-garlic, high-Se wheat, selenoethionine, dimethyl selenide, dimethyl selenoxide, selenite, or mixtures thereof.

Boron is an element commonly found in the human diet. An average Western diet provides approximately 1-2 mg of boron per day and the median intake of boron for adults is approximately 1.0 to 1.5 mg/day. Borates have been used to treat epilepsy at doses between 1 g/day of boric acid (2.5 mg/kg/day) to 25 g/day of boric tartrate (24.8 mg/kg/day). High concentrations of boron in the drinking water in Turkey did not cause any deleterious effects in humans exposed over many generations.

Boric acid can inhibit a wide variety of enzymes in vitro, including serine proteases such as prostate-specific antigen, thrombin, factor Xa, kallikrein, elastase, plasmin, prolyl endopeptidase, and Ig AI protease. Boric acid inhibits the growth of several prostate and breast cancer cell lines, but the inhibition mechanism is not exactly known. Boric acid inhibits proliferation, adhesion, migration and invasiveness of prostate cancer cells. Myeloma cell lines and mantle cell lines have a much greater sensitivity to proteasome inhibition compared to normal peripheral blood mononuclear cells and most other cancer cell lines.

A limited epidemiological study in American men found that increased dietary boron intake was associated with a decreased risk of prostate cancer. Another study found that increased boron concentrations in groundwater in the state of Texas were correlated with reduced risk of prostate cancer.

Boric acid improves the anti-proliferative effectiveness of chemo-preventative agents, selenomethionine and genistein, while enhancing the cell killing by ionizing radiation. The combination of boric acid with ascorbic acid is able to inhibit DNA synthesis and has antitumor activity.

In the practice of the present invention, although boric acid and boric acid salts are preferred compounds, alternative borates, boranes and boron compounds could be used. These alternative compounds include: organic boron compounds, carboxyborane adducts of Lewis bases (e.g., boron analogs of α-amino acids) and amide and ester derivatives thereof, metal complexes of such Lewis base-carboxyborane adducts and their amide and ester derivatives, bortezomib([(1R)-3-methyl-1-({(2S)-3-phenyl-2-[(pyrazin-2-ylcarbonyl)amino] propanoyl}amino)butyl]boronic acid; marketed as Velcade by Millennium Pharmaceuticals).

Minerals can be provided in a variety of forms. Preferred forms of minerals are generally those that are administered orally and are more absorbable. Magnesium can be provided in a variety of forms and with various counter ions, including among others magnesium citrate, magnesium fumarate, magnesium gluconate, magnesium α-ketoglutarate, magnesium lactate, magnesium malate, magnesium succinate, magnesium picolinate, magnesium sulphate or mixtures thereof, such as magnesium Krebs in which the counter ions are a mixture of the anions of the five primary organic acids of the tricarboxylic acid cycle (Krebs Cycle) i.e., a mixture of the magnesium salts of citric, fumaric, malic, α-ketoglutaric and succinic acids.

Zinc is believed to play a significant role as an antioxidant and is associated with protection against lipid peroxidation in retinal and epithelial vascular tissue, possibly due to its enhancement of superoxide dismutase function. Zinc has an anti-copper effect by blocking the absorption of copper and increasing copper excretion in the stool. This translates into an antiangiogenic effect on tumors. Zinc has positive effects in reducing an enlarged prostate. Zinc has anti-inflammatory effect on the prostate, prevents prostate cancer, and improves the immune system. Studies have indicated that when zinc is administered orally, it is difficult to reach the prostatic tissue, therefore the prostate does not reap the full benefits of the zinc. Zinc can include zinc gluconate, zinc acetate, zinc oxide, or any salt that contains the Zn2+ ion.

Natural Extracts

Many natural products, herbs, extracts, vitamins and minerals can enhance the effectiveness of conventional anticancer therapies or are effective against cancer by themselves. They help the body fight the growth of cancer and progression of cancer or other diseases, assist in slowing, stopping, or reversing the growth of some cancers, bolster or improve the body's resistance to certain life threatening conditions, and reduce the negative side-effects of cancer, cancer treatment and other diseases and their treatments. Some natural products slow, stop, or reverse the growth of cancer cells and/or promote and strengthen the human body's own immune defense against cancer. Additionally, they may allow cancer victims to maintain a significantly higher health status, as defined by mobility, weight gain and energy level during treatment and post treatment.

Essiac Tea or its variations is a multi-herb tea that may contain burdock root (*Arcticum lappa*), sheep sorel (*Rumex acetosella*), slippery elm bark (*Ulmus rubra* or *Ulmus fulva*), Turkish or Indian rhubarb root (*Rheum palmatum*). It has anticancer activity and helps with healing and maintaining the liver.

Saw palmetto (*Serenoa repens*) or dwarf palm plant is a small shrubby palm tree found in the southeastern United States. The lipophilic extract of saw palmetto berries contains sterols, phytosterols (β-sitosterol and its glucosides, stigmasterol, campesterol), fatty acids (lauric, myristic, oleic, linoleic, linolenic acids) and fatty alcohols (docosanol, hexacosanol, octacosanol, triacontanol). The lipophilic extract of *Serenoa repens* has been used in the treatment of prostate cancer and was shown to be effective in the treatment of benign prostate hypertrophy (BPH). It effectively reduces the size of the enlarged prostate, reduces prostatic inflammation and swelling, improves uncomfortable urinary symptoms: improves urinary flow, reduces residual bladder urine volume, increases ease in commencing urination, decreases frequency of urination and decreases the need to empty the bladder at night. Treatments with *Serenoa repens* are very well tolerated and do not have any significant adverse side-effects [22].

Saw palmetto extracts, mainly through fatty acids such as lauric and myristic acids, were shown to inhibit the testosterone 5α-reductase, thereby reducing the conversion of testosterone to 5-α dihydrotestosterone. The levels of dihydrotestosterone are significantly higher in men with BPH. *Serenoa repens* does not directly inhibit the secretion of prostate specific antigen (PSA) into the blood, which allows the continued use of this prostate cancer marker for monitoring men under treatment. *Serenoa repens* extracts are also able to induce apoptosis in prostate epithelial and stromal cells. Saw palmetto also inhibits cycloxygenase and 5-lipoxygenase, which explains its anti-inflammatory activity.

Proteases

Bromelain is a mixture of colloids (including proteins, carbohydrates and mucopolysaccharides), inorganic salts and simpler organic materials obtained from pineapple (*Ananas comosus*). It contains at least two proteolytic enzymes and other non-proteolytic enzymes, such as acid phosphatase, peroxidase, amylase, cellulase. The principle component of the extract is the glycoprotein proteolytic enzyme, bromelain. Papain is a proteolytic enzyme obtained from the *Carica papaya*, which also contains chymopapain. Trypsin is a proteolytic enzyme formed in the pancreas. These proteases can also be prepared by recombinant means.

Proteases have many uses. In medicine, they are commonly used as digestive aids, for supporting enzymatic digestion, and for wound healing. They have anti-inflammatory activity, inhibit platelet aggregation, and inhibit prostaglandins. These proteases have been in clinical use for over 30 years and have no harmful side effects even with prolonged use.

Transfer factor (TF) is a dialyzed extract from leukocyte homogenate of human or other origin. TF is a natural immunomodulator that influences cell-mediated immunity. It can be used as a stimulator of cell-mediated immune response in many diseases caused by immune deficiencies, malignancies, or bacterial, viral, and fungal infections. TF contains a mixture of biologically active substances with molecular weights less than 10 kDa. TF's chemical structure is not defined yet, but evidence suggests that it is a small peptide attached to ribonucleotides. TF is non-species specific, resistant to proteolytic enzymes and able to survive oral administration. Its mechanisms of action are not clear. TF is non-toxic and its administration has no side effects. TF has been used as an adjuvant in the cancer therapy of Burkitt's lymphoma, nasopharyngeal carcinoma and urological neoplasias. TF was reported to help in the therapy of malignant melanoma and osteogenic sarcoma.

The therapeutical method of this invention can be used for the treatment, amelioration, inhibition or prevention of a disease of cell proliferation and differentiation, such as viral diseases and neoplasias. The neoplasias can be carcinomas, sarcomas, melanomas, hematological neoplasias or other neoplasias. The carcinomas can be of various types and origins, such as adrenocortical carcinoma, adenoid cycstic carcinoma, adenosquamous carcinoma, bartholin gland carcinoma, basal cell carcinoma, bartholin gland carcinoma, bile duct carcinoma, bladder carcinoma and adenocarcinoma, bronchial gland carcinomas, bronchogenic carcinoma, capillary carcinoma, carcinoids, malignant carcinoid, carcinoma of unknown primary site, cavernous carcinoma, cholangiocarcinoma, choriocarcinoma, choriod plexus papilloma/carcinoma, clear cell carcinoma, cystadenocarcinoma, embryonal carcinoma, endodermal sinus tumor (infantile embryonal carcinoma), endometrioid adenocarcinoma, epidermoid carcinomas, epithelial carcinomas, hepatocellular carcinoma, in situ carcinoma, islet cell carcinoma, large cell carcinoma, large-cell neuroendocrine carcinoma (of the lung), lung carcinoma, small cell lung carcinoma, mammary adenocarcinoma, medullary carcinoma, medullary carcinoma of the thyroid, meningeal, mesothelial, metastatic carcinoma, Merkel cell carcinoma, mucoepidermoid carcinoma, metastatic skin carcinoma, neuroendocrine carcinoma, neuroendocrine carcinoma of the cervix, neuroepithelial adenocarcinoma, oat cell carcinoma, ovarian carcinoma, papillary serous adenocarcinoma, papillary adenocarcinomas, papillary carcinoma, prostatic adenocarcinoma, renal cell carcinoma, renal cell tumor, respiratory tract carcinomas, sebaceous gland carcinoma, serous carcinoma, skin carcinoma, small cell carcinoma, soft tissue carcinomas, squamous cell carcinoma of both ulcerating and papillary type, invasive squamous cell carcinoma, squamous carcinoma, squamous cell carcinomas of the mouth, throat, larynx, and lung; intraepithelial neoplasia, interepithelial squamous cell neoplasia, sweat gland carcinoma, thymoma, malignant thymoma and thymic carcinoma, undifferentiated carcinoma, verrucous carcinoma, poorly-differentiated neuroendocrine carcinoma (high-grade malignant carcinoid), well differentiated carcinoma, well-differentiated neuroendocrine carcinoma (malignant carcinoid), and other carcinomas. The sarcomas can be adenosarcoma, angiosarcoma, carcinosarcoma, chondrosarcoma, clear cell sarcoma, cystosarcoma phyllodes (phyllodes tumor), endometrial stromal sarcoma, endotheliosarcoma, Ewing's sarcomas, fibrosarcoma, gliosarcoma, granulocytic sarcoma, hemangiosarcoma, Kaposi's sarcoma, leiomyosarcoma, liposarcoma, lymphangiosarcoma, lymphangioendotheliosarcoma, mast cell sarcoma, meningeal sarcoma, myxosarcoma, osteogenic sarcoma, osteosarcoma, pseudosarcoma, rhabdomyosarcoma, sarcomas of bone and soft tissue, soft tissue sarcoma, uterine sarcoma, veticulum cell sarcoma, and other sarcomas. The melanomas can be melanoma in the skin such as superficial spreading melanoma, nodular melanoma, lentiginous skin melanoma, acral lentiginous melanoma, lentigo maligna melanoma; other melanomas, such as clear cell sarcoma (melanoma of soft parts), mucosal melanoma, uveal (intraocular) melanoma.

The hematological neoplasias can be leukemias and leukemia-related disorders, such as acute and chronic lymphocytic (lymphoblastic) leukemias, acute and chronic myelogenous (myeloid, myelocytic) leukemias, hairy cell leukemia; myeloma and multiple myeloma; lymphomas, such as Hodgkin's disease (classical Hodgkin's lymphoma, such as nodular sclerosing CHL, mixed-cellularity subtype, lymphocyte-rich, lymphocyte depleted or not depleted; non-classical Hodgkin's lymphoma such as nodular lymphocyte-predominant Hodgkin's lymphoma) or non-Hodgkin lymphoma (many subtypes); mature B cell neoplasms: chronic lymphocytic leukemia/small lymphocytic lymphoma, B-cell prolymphocytic leukemia, lymphoplasmacytic lymphoma (such as Waldenström macroglobulinemia or primary macroglobulinemia), splenic marginal zone lymphoma, plasma cell neoplasms (plasma cell myeloma, plasmacytoma, monoclonal immunoglobulin deposition diseases, heavy chain diseases), extranodal marginal zone B cell lymphoma, also called MALT lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, Burkitt lymphoma/leukemia, primary cerebral lymphoma; mature T-cell and natural killer (NK) cell neoplasms: T-cell prolymphocytic leukemia, T-cell large granular lymphocytic leukemia, aggressive NK cell leukemia, adult T-cell leukemia/lymphoma, extranodal NK/T-cell lymphoma, nasal type, enteropathy-type T cell lymphoma, hepatosplenic T cell lymphoma, blastic NK cell lymphoma, mycosis fungoides/Sezary syndrome, cutaneous T-cell lymphoma, primary cutaneous CD30-positive T cell lymphoproliferative disorders (primary cutaneous anaplastic large cell lymphoma, lymphomatoid papulosis), angioimmunoblastic T cell lymphoma, peripheral T cell lymphoma, unspecified, anaplastic large cell lymphoma; immunodeficiency-associated lymphoproliferative disorders, associated with a primary immune disorder, associated with the Human Immunodeficiency Virus (HIV), immunoblastic lymphoma, post-transplant, associated with methotrexate therapy (chemotherapy), primary cerebral lymphoma also known as primary CNS lymphoma, central nervous system lymphoma, acute and chronic lymphocytic and granulocytic tumors; myelodysplastic-myeloproliferative such as juvenile myelomonocytic leukemia and chronic myelomonocytic leukemia; mast cell tumor: mast cell leukemia, systemic mastocytosis, reactive diseases of Langerhans cells, such as histiocytomas, cutaneous histiocytosis, systemic histiocytosis; malignant diseases of Langerhans dells, such as malignant histiocytosis, diffuse histiocytic sarcoma, localized histiocytic sarcoma; reactive diseases of macrophages, such as hemophagocytic lymphohistiocytosis; malignant diseases of macrophages such as histiocytic lymphoma, and other haematological neoplasms. The neoplasia can also be a benign tumor, such as a cyst, polyp, fibroid tumor, endometriosis, benign prostatic hypertrophy and prostatic intraepithelial neoplasia.

This application is an integrated description of the invention as a whole, not merely of any particular element or facet thereof. Although the present invention has been described with reference to specific details, it is not intended that such detail should be regarded as limitations upon the scope of the invention. This publication describes the best mode known to the authors for carrying out the invention and one of skill in the art should be fully able to practice the invention upon reading the detailed description. While the present invention is described and exemplified with some specificity, those skilled in the art will appreciate the various modifications, including variations, additions, and omissions, that may be made in what has been described. Such modifications and variations are not departing from the scope of the invention. The inventors expect skilled artisans to employ such variations as appropriate, and the inventors intend for the invention to be practiced otherwise than as specifically described herein. It is intended that these modifications also be encompassed by the present invention and that the scope of the present invention be limited solely by the broadest interpretation lawfully accorded to the appended claims.

U.S. Pat. No. 6,559,139 by Johnson at al. [23] describes the administration of vitamin D derivatives with other cytotoxic agents. In that patent, the cytotoxic agent is used for its cancer cell killing ability and it is administered at doses needed for that activity. Johnson et al. teach the doses of cytotoxic agent at which the agent is cytotoxic to cancer cells. Those doses are very different than the doses used in our method. The method of our invention uses administration of the cytotoxic agents cyclophosphamide, 5'-fluorouracil and methotrexate in low doses, administered often and at relatively short time intervals, such as every day. This administration is different than the normal administration of these drugs to cancer patients, where they are administered for their cytotoxic effects on cancer cells (administration of large doses separated by multiple days for recovery—bolus administration). The low-dose administration of these drugs changes their mechanism of action on cancer: at high doses these drugs kill the cancer cells directly through their cytotoxic effect; at low doses they modify the tumor environment by acting on non-cancerous cells in the tumor bed and resulting in activation of anticancer immunity and reduction of newly formed blood vessels that feed the tumor (antiangiogenic effect). The effect of cyclophosphamide, 5'-fluorouracil and methotrexate at low concentrations is unexpected and it is enhanced by simultaneous administration of the nuclear receptor ligands: retinoic acid, phenylacetic acid and vitamin D derivatives.

Any of the compounds from the method of our invention, used by itself in the low doses specified by our invention, would be ineffective in cancer treatment. In order to be effective, cyclophosphamide, 5'-fluorouracil and methotrexate have to be administered to cancer patients at much higher doses than those used in the present invention. For example, the recommended doses for a 28-day cycle CMF regimen (cyclophosphamide/methotrexate/5-fluorouracil) for breast cancer patients are 100 mg/m$^2$ cyclophosphamide p.o. days 1 through 14 (equivalent to 160 mg for an average 60 kg female); 40 mg/m$^2$ methotrexate i.v. day 1, 8 (equivalent to 64 mg for an average 60 kg female); and 600 mg/m$^2$ 5-fluorouracil i.v. day 1, 8 (equivalent to 960 mg for an average 60 kg female). There is no indication in the current literature that combining these compounds at low doses with nuclear receptor ligands, such as retinoids and vitamin D derivatives, would result in an enhanced anticancer effect.

The present invention is further supported by the following example. This example is presented for purely illustrative purposes and it should not be used to construe the scope of the invention in a limiting manner.

EXAMPLE

Treatment of a Patient with Breast Cancer

A 58-year old woman presented with breast cancer characterized by biopsy and anatomopathological exam as infiltrating ductal carcinoma associated with high nuclear grade, poorly differentiated comedocarcinoma, with necrosis area of 2.8 cm diameter and atypical lymphatic vessels. The tumor diameter was 8 cm and the patient suffered pain. The patient weighed 60 kg and was orally administered the following drugs daily: 60 mg cyclophosphamide, 100 mg capecitabine (pentyl[1-(3,4-dihydroxy-5-methyl-tetrahydrofuran-2-yl)-5-fluoro-2-oxo-1H-pyrimidin-4-yl]aminomethanoate), 6 mg methotrexate, 0.75 µg 1α,25-dihydroxyvitamin D3, 200 mg all-trans retinoic acid, 200 mg N-(4-hydroxyphenyl) retinamide (Fenretinide), 2 g phenylacetic acid, 5.2 mg prednisolone, 300 mg 7-hydroxycoumarin, 15 mg vitamin K, 100 mg L-3,4-dihydroxyphenylalanine (Levodopa), 25 mg Carbidopa, 300 mg hydroquinone, 80 mg metol, 150 mg rutin, 1.2 g vitamin E, 600 mg β-carotene, 420 mg silymarin, 12.5 mg boric acid, 25 mg borax, and 400 mg selenomethionine. After 1 month of combination therapy of this invention the pain subsided and the tumor diameter was reduced to 7 cm. Four months into therapy, the tumor was 6.5×5 cm. Six months into therapy, the tumor lump could not be detected by manual examination, the nipple reverted to normal position, and tumor markers CEA, CA15-3 and CA27-29 had normal values. CT scan confirmed tumor disappearance. During therapy, the blood tests were within normal values: leukocytes 5300 to 6000, erythrocytes 5 to 6 million, monocytes 5-6%. During and after therapy, the patient did not exhibit secondary symptoms of neoplasia and side effects caused by the treatment. Six and 12 month after the end of therapy (when cancer could not be detected) the patient was administered the combination therapy for other 2 months, in order to decrease the probability of remission (prevention of possible remission). Five years after initiation of therapy, the patient was alive and cancer-free.

1. Bocci, G., K. C. Nicolaou, and R. S. Kerbel, *Protracted low-dose effects on human endothelial cell proliferation and survival in vitro reveal a selective antiangiogenic window for various chemotherapeutic drugs.* Cancer Research, 2002. 62(23): p. 6938-6943.
2. Browder, T., C. E. Butterfield, B. M. Kraling, B. Shi, B. Marshall, M. S. O'Reilly, and J. Folkman, *Antiangiogenic scheduling of chemotherapy improves efficacy against experimental drug-resistant cancer.* Cancer Research, 2000. 60(7): p. 1878-1886.
3. Bertolini, F., S. Paul, P. Mancuso, S. Monestiroli, A. Gobbi, Y. Shaked, and R. S. Kerbel, *Maximum tolerable dose and low-dose metronomic chemotherapy have opposite effects on the mobilization and viability of circulating endothelial progenitor cells.* Cancer Research, 2003. 63(15): p. 4342-4346.
4. Colleoni, M., A. Rocca, M. T. Sandri, L. Zorzino, G. Masci, F. Nole, G. Peruzzotti, C. Robertson, L. Orlando, S. Cinieri, F. de Braud, G. Viale, and A. Goldhirsch, *Low-dose oral methotrexate and cyclophosphamide in metastatic breast cancer: antitumor activity and correlation with vascular endothelial growth factor levels.* Annals of Oncology, 2002. 13(1): p. 73-80.
5. Klement, G., S. Baruchel, J. Rak, S. Man, K. Clark, D. J. Hicklin, P. Bohlen, and R. S. Kerbel, *Continuous low-dose therapy with vinblastine and VEGF receptor-2 antibody induces sustained tumor regression without overt toxicity.* Journal of Clinical Investigation, 2000. 105(8): p. R15-R24.
6. Kakeji, Y. and B. A. Teicher, *Preclinical studies of the combination of angiogenic inhibitors with cytotoxic agents.* Investigational New Drugs, 1997. 15(1): p. 39-48.
7. Berd, D., H. C. Maguire, and M. J. Mastrangelo, *Potentiation of human cell-mediated and humoral immunity by low-dose cyclophosphamide.* Cancer Research, 1984. 44(11): p. 5439-5443.
8. Munoz, R., S. Man, Y. Shaked, C. R. Lee, J. Wong, G. Francia, and R. S. Kerbel, *Highly efficacious nontoxic preclinical treatment for advanced metastatic breast cancer using combination oral UFT-cyclophosphamide metronomic chemotherapy.* Cancer Research, 2006. 66(7): p. 3386-3391.
9. Berd, D. and M. J. Mastrangelo, *Effect of low dose cyclophosphamide on the immune system of cancer patients: reduction of T-suppressor function without depletion of the CD8+ subset.* Cancer Res., 1987. 47(12): p. 3317-21.
10. Pili, R., M. P. Kruszewski, B. W. Hager, J. Lantz, and M. A. Carducci, *Combination of phenylbutyrate and 13-cis retinoic acid inhibits prostate tumor growth and angiogenesis.* Cancer Research, 2001. 61(4): p. 1477-1485.
11. Carducci, M. A., J. Gilbert, M. K. Bowling, D. Noe, M. A. Eisenberger, V. Sinibaldi, Y. Zabelina, T. L. Chen, L. B. Grochow, and R. C. Donehower, *A Phase I clinical and pharmacological evaluation of sodium phenylbutyrate on an 120-h infusion schedule.* Clin Cancer Res., 2001. 7(10): p. 3047-55.
12. Gilbert, J., S. D. Baker, M. K. Bowling, L. Grochow, W. D. Figg, Y. Zabelina, R. C. Donehower, and M. A. Carducci, *A phase I dose escalation and bioavailability study of oral sodium phenylbutyrate in patients with refractory solid tumor malignancies.* Clinical Cancer Research, 2001. 7(8): p. 2292-2300.
13. Gore, S. D., L. J. Weng, W. D. Figg, S. P. Zhai, R. C. Donehower, G. Dover, M. R. Greyer, C. Griffin, L. B. Grochow, A. Hawkins, K. Burks, Y. Zabelena, and C. B. Miller, *Impact of prolonged infusions of the putative differentiating agent sodium phenylbutyrate on myelodysplastic syndromes and acute myeloid leukemia.* Clinical Cancer Research, 2002. 8(4): p. 963-970.
14. Jones, G., S. A. Strugnell, and H. F. DeLuca, *Current understanding of the molecular actions of vitamin D.* Physiological Reviews, 1998. 78(4): p. 1193-1231.
15. Majewski, S., A. Szmurlo, M. Marczak, S. Jablonska, and W. Bollag, *Inhibition of tumor cell-induced angiogenesis by retinoids, 1,25-dihydroxyvitamin-D3 and their combination.* Cancer Letters, 1993. 75(1): p. 35-39.
16. Yu, W. D., M. C. McElwain, R. A. Modzelewski, D. M. Russell, D. C. Smith, D. L. Trump, and C. S. Johnson, *Enhancement of 1,25-dihydroxyvitamin D-3-mediated antitumor activity with dexamethasone.* Journal of the National Cancer Institute, 1998. 90(2): p. 134-141.
17. Grant, W. B. and C. R. Garland, *A critical review of studies on vitamin D in relation to colorectal cancer.* Nutrition and Cancer—an International Journal, 2004. 48(2): p. 115-123.
18. Molnar, J., N. Gyemant, I. Mucsi, A. Molnar, M. Szabo, T. Kortvelyesi, A. Varga, P. Molnar, and G. Toth, *Modulation of multidrug resistance and apoptosis of cancer cells by selected carotenoids.* In Vivo, 2004. 18(2): p. 237-244.
19. Weber, T., M. Lu, L. Andera, H. Lahm, N. Gellert, M. W. Fariss, V. Korinek, W. Sattler, D. S. Ucker, A. Terman, A. Schroder, W. Erl, U. T. Brunk, R. J. Coffey, C. Weber, and J. Neuzil, *Vitamin E succinate is a potent novel antineoplastic agent with high selectivity and cooperativity with tumor necrosis factor-related apoptosis-inducing ligand (Apo2 ligand) in vivo.* Clinical Cancer Research, 2002. 8(3): p. 863-869.
20. *The effect of vitamin E and beta carotene on the incidence of lung cancer and other cancers in male smokers. The Alpha-Tocopherol, Beta Carotene Cancer Prevention Study Group.* N Engl J Med., 1994. 330(15): p. 1029-35.
21. Jacobs, E. J., A. K. Henion, P. J. Briggs, C. J. Connell, M. L. McCullough, C. R. Jonas, C. Rodriguez, E. E. Calle, and M. J. Thun, *Vitamin C and vitamin E supplement use and* bladder cancer mortality in a large cohort of US men and women. American Journal of Epidemiology, 2002. 156 (11): p. 1002-1010.

22. Wilt, T. J., A. Ishani, G. Stark, R. MacDonald, J. Lau, and C. Mulrow, *Saw palmetto extracts for treatment of benign prostatic hyperplasia—A systematic review*. Jama-Journal of the American Medical Association, 1998. 280(18): p. 1604-1609.

23. Johnson, C. S. and D. L. Trump, *Combination chemotherapy*, U.S. Pat. No. 6,559,139, 2003.

What is claimed is:

1. A method for treatment of breast cancer in a human woman in need thereof, which comprises administering to said woman of 20 to 100 mg/day cyclophosphamide, 50 to 500 mg/day capecitabine (pentyl[1-(3,4-dihydroxy-5-methyl-tetrahydrofuran-2-yl)-5-fluoro-2-oxo-1H-pyrimidin-4-yl]aminomethanoate; Xeloda), 2 to 10 mg/day methotrexate, 20 to 500 mg/day N-(4-hydroxyphenyl) retinamide (Fenretinide), and 0.25 to 1.5 µg/day 1α,25-dihydroxyvitamin D3 (calcitriol).

2. The method of claim 1, further comprising administering 1 to 10 g/day phenylacetic acid.

3. The method of claim 1, further comprising administering 2 to 10 mg/day prednisolone.

4. The method of claim 1, further comprising administering 10 to 25 mg/day vitamin K.

5. The method of claim 1, further comprising administering 0.1 to 1 g/day 7-hydroxycoumarin.

6. The method of claim 1, further comprising administering 100 to 200 mg/day L-3,4-dihydroxyphenylalanine.

7. The method of claim 1, further comprising administering 200 to 400 mg/day hydroquinone.

8. The method of claim 1, further comprising administering 20 to 100 mg/day metol.

9. The method of claim 1, further comprising administering 0.1 to 0.5 g/day rutin.

10. The method of claim 1, further comprising administering 0.4 to 1.6 g/day vitamin E.

11. The method of claim 1, further comprising administering 0.2 to 1 g/day n-carotene.

12. The method of claim 1, further comprising administering 10 to 20 mg/day boric acid and 20 to 50 mg/day borax.

13. The method of claim 1, further comprising administering 0.2 to 1 g/day selenomethionine.

14. The method of claim 1, further comprising administering 0.4 to 2 g/day silymarin.

* * * * *